(12) United States Patent
Jackson

(10) Patent No.: US 8,092,665 B2
(45) Date of Patent: Jan. 10, 2012

(54) EXPANDING CAM LOCK FOR SEALING SLAB GELS IN AN ELECTROPHORESIS APPARATUS

(75) Inventor: Tom R. Jackson, La Jolla, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1402 days.

(21) Appl. No.: 11/404,985

(22) Filed: Apr. 14, 2006

(65) Prior Publication Data

US 2006/0254918 A1    Nov. 16, 2006

Related U.S. Application Data

(60) Provisional application No. 60/671,757, filed on Apr. 15, 2005, provisional application No. 60/711,919, filed on Aug. 26, 2005.

(51) Int. Cl.
*G01N 27/447* (2006.01)
*G01N 27/453* (2006.01)

(52) U.S. Cl. ......... 204/618; 204/606; 204/467; 204/456

(58) Field of Classification Search .................. 204/456, 204/450, 467, 606, 618, 600; 269/66, 71, 269/70, 73, 77, 84, 85, 196–207, 229–233
See application file for complete search history.

(56) References Cited

U.S. PATENT DOCUMENTS 6,001,233 A    12/1999    Levy

FOREIGN PATENT DOCUMENTS

| WO | WO-2004/047984 | 8/2000 |
|---|---|---|
| WO | WO-02/092200 | 11/2002 |
| WO | WO-2005/031332 | 4/2005 |
| WO | WO-2006/113365 | 10/2006 |

OTHER PUBLICATIONS

EP 06750059.5; Office Action Mailed Jul. 26, 2010.
Invitrogen Life Technologies, "Xcell SureLock Mini-Cell: The Most Convenient, Versatile, Mini-Vertical Electrophoresis System", www.invitrogen.com/content.cfm?, pageid=3476&cfid=1359647 &cftoken=23915763, Apr. 18, 2001, 1-5.
PCT/US06/13895; International Search Report mailed on Nov. 12, 2006.
PCT/US06/13895; Written Opinion mailed on Oct. 15, 2007.

*Primary Examiner* — Gurpreet Kaur

(57) ABSTRACT

An expanding cam lock for use with an electrophoresis system is disclosed herein. The cam lock allows the simultaneous use of multiple slab gel cassettes in first and second buffer core assemblies in an electrophoresis system while maintaining the necessary compressive force to create a liquid-tight seal between the anode and cathode buffer solutions. In one example embodiment, the expanding cam lock includes a base plate with a first surface adapted to engage the first buffer core assembly and a follower plate having second surface adapted to engage the second buffer core assembly, buffer dam or buffer displacement dam. The base plate and the follower plate are slidably coupled together and are designed for insertion between the first buffer core assembly and the second buffer core assembly, buffer dam or buffer displacement dam in the electrophoresis container. A cam is positioned between and moveably coupled with the base plate and the follower plate. The cam is movable from a first position to a second position to urge the first and second surfaces to secure the gel cassette to the first and second buffer core assemblies. Also provided herein is a buffer displacement dam. Also provided herein are kits and assemblies which incorporate the expanding cam and buffer displacement dam described herein.

28 Claims, 6 Drawing Sheets

EXPANDING CAM LOCK FOR SEALING SLAB GELS IN AN ELECTROPHORESIS APPARATUS

CROSS-REFERENCE TO RELATED APPLICATION

This application claims the benefit of U.S. Provisional Application Ser. No. 60/671,757, filed on Apr. 15, 2005, and U.S. Provisional Application Ser. No. 60/711,919, filed on Aug. 26, 2005, the disclosures of which are hereby incorporated by reference in their entirety.

TECHNICAL FIELD

The present invention relates generally to an apparatus for performing electrophoresis. More particularly, the present invention relates to an expanding cam lock for clamping and sealing slab gel cassettes in a gel electrophoresis system during electrophoresis. The present invention also relates to a displacement dam for use in a gel electrophoresis apparatus or an electrophoretic transfer apparatus that occupies space in a buffer chamber of the apparatus such that less volume of buffer is required than would otherwise be used. A displacement dam is particularly useful when performing electrophoresis using fewer than the maximum number of gel cassettes than can be accommodated by the electrophoresis apparatus or electrophoretic transfer ("electroblotting") apparatus.

BACKGROUND

Gel electrophoresis is commonly used to separate, by molecular size, biological molecules, such as deoxyribonucleic acid ("DNA"), ribonucleic acid ("RNA") and proteins. To perform gel electrophoresis, a polymeric gel, such as polyacrylamide, is formed in a glass tube, or between spaced glass or plastic plates. The tube or plates are then placed in a container along with anode and cathode elements at the top and bottom of the gel. Sample wells formed in the top of the gel are first filled with buffer solutions. Molecule samples prepared in a sample buffer that may contain a tracking dye are then placed in the wells. Electrophoretic buffer solutions containing conductive ions are added to the container to make electrical contact between the gel, the samples in the wells and the anode and cathode elements. A voltage is then applied across the gel, which causes the sample molecules and any tracking dye to migrate toward the bottom of the gel, and separate into bands whose migration distance depends on molecular size.

For accurate electrophoretic separation, the first and second buffer solutions must be isolated from one another. To provide isolation, electrophoresis systems use various methods to hold the gel cassettes in contact with the buffer core and secure the buffer core assembly in the container. Previously known electrophoresis systems commonly use a buffer core subassembly containing clamps or latches that secure the gel cassettes to the buffer core.

Gel electrophoresis systems, such as the XCell Sure-Lock™ Mini-Cell system manufactured by Invitrogen Corporation, of San Diego, Calif., or the electrophoresis system described in U.S. Pat. No. 6,001,233, include a container for receiving a first buffer solution and a buffer core assembly for receiving a second buffer solution. The buffer core assembly comprises a pair of gel cassettes affixed to front and back sides of a U-shaped buffer core body forming a buffer core assembly. The space defined by the upraised side members of the buffer core body and the end faces of the gel cassettes forms an upper buffer chamber. Once the cassettes are secured, the buffer core assembly is loaded in the electrophoresis container toward one end prior to electrophoretic separation. A cam-activated clamp is then inserted into an electrophoresis container near the other end, between the buffer core assembly and the back wall of the container. A cam on the cam-activated clamp is disposed to engage a back wall of the container to cause a mounting block to apply uniform pressure to secure the gel cassettes to the buffer core body. Since there is only one mounting block, this electrophoresis system is limited to one buffer core assembly with a maximum of two gel cassettes. If a second buffer core assembly is positioned on the cam side of the cam activated clamp, the cam may deform the gel cassette in contact with the cam, and this deformation of the gel cassette may allow leakage of the buffer solution from the upper buffer chamber in the second buffer core assembly.

In view of the practical limitations associated with prior art clamping methods and apparatus, it is desirable to provide a cam-activated lock that requires no clamping subassembly and is positioned between two buffer core assemblies to reliably secure electrophoresis gel cassettes in each of the buffer core assemblies. It is further desirable to provide a cam-activated lock that provides a consistent and reproducible clamping force each time the apparatus is used.

Another issue for users of gel electrophoresis apparatuses that can accommodate multiple buffer cores is the unnecessary use of large volumes of buffer when fewer than the maximum number of gels are run in the apparatus.

Furthermore, in certain aspects, provided herein is an apparatus for electrophoresis or electrophoretic transfer of biomolecules that that includes a buffer displacement dam in at least one buffer reservoir of the apparatus. The buffer displacement dam is a solid or partially or substantially hollow or open structure that conforms to the size of the interior of the buffer reservoir in at least one dimension, and replaces the space which would otherwise be occupied by buffer contained within the buffer reservoir during electrophoretic separation or transfer of biomolecules.

SUMMARY OF THE INVENTION

An expanding cam lock is described herein for simultaneously running a plurality of gels or electrophoretic strips, including but not limited to slab gels and slab gel cassettes, in buffer core assemblies within an electrophoresis system while maintaining the necessary compressive force to create a liquid-tight seal in the buffer core assemblies to keep the anode and cathode buffer solutions separate.

An aspect of the expanding cam lock described herein, used for sealing at least one gel cassette in an electrophoresis apparatus, is an expanding cam lock which comprises a base plate having a first surface adapted to engage a buffer core assembly comprising at least one electrophoresis gel cassette; a follower plate having a second surface adapted to engage a partition assembly, and a cam positioned between and moveably coupled with the base plate and the follower plate; wherein, the base plate and the follower plate are slideably coupled together and configured for insertion between the buffer core assembly and the partition assembly in the electrophoresis apparatus, and the cam being movable from a first position to a second position to urge the first surface toward the electrophoresis gel cassette of the buffer core assembly and the second surface toward the partition assembly thereby sealing at least one electrophoresis gel cassette to the buffer core assembly within the electrophoresis apparatus.

In an embodiment of this aspect, the partition assembly comprises a buffer dam, a buffer displacement dam, or a buffer core assembly comprising at least one electrophoresis gel cassette. In a further or alternative embodiment, the cam is pivotally coupled to the base plate and is configured to slideably engage the follower plate. In a further or alternative embodiment, the cam includes axle pins pivotally coupling the cam to the base plate. In a further or alternative embodiment, the cam is configured to lock the base plate into engagement with the electrophoresis gel cassette of the buffer core and the follower plate into engagement with the partition assembly when the cam is in the second position. In a further or alternative embodiment, the cam includes a push bar configured to engage the base plate to prevent further urging of the first surface toward the buffer core assembly and the second surface toward the partition assembly. In a further or alternative embodiment, the cam includes a handle to pivot the cam relative to the base plate and follower plate. In a further or alternative embodiment, the cam further has a curved end that slidingly engages the follower plate. In a further or alternative embodiment, the first and second surfaces include push tabs adapted to facilitate urging of the first surface toward the buffer core assembly and the second surface toward the partition assembly. In a further or alternative embodiment, the base plate includes first side panels on a reverse side opposing the first surface and the follower plate includes second side panels on a reverse side opposing the second surface, the first and second side panels being coupled together. In a further or alternative embodiment, the first side panels include slots and the second side panels include lever arms with locking portions configured to slideably engage the slots.

In further or alternative embodiments, the base plate, follower plate, partition assembly, and cam are made of a polymer selected from the group consisting of styrene acrylonitrile, polycarbonate, polystyrene, acrylic, acrylate, polymethyl methacrylate, polyethylene, high density polyethylene, polyethylene terephthalate, glycol-modified polyethylene terephthalate, polypropylene, polyoxymethylene, Acetel and copolymers thereof. In further or alternative embodiments, the base plate, follower plate, partition assembly, and cam are fabricated by a molding technique. In a further or alternative embodiment, the molding technique is injection molding. In a further or alternative embodiment, the base plate, follower plate, partition assembly, and cam are fabricated by machining.

In an aspect of the expanding cam described herein is an expanding cam lock for sealing gel cassettes in first and second buffer core assemblies in an electrophoresis container, wherein the expanding cam lock includes a base plate having a first surface adapted to engage the first buffer core assembly; a follower plate having second surface adapted to engage the second buffer core assembly, the base plate and the follower plate being slideably coupled together and configured for insertion between the two buffer core assemblies in the electrophoresis container; and a cam positioned between and moveably coupled with the base plate and the follower plate, the cam being movable from a first position to a second position to urge the first and second surfaces to secure the gel cassettes to the first and second buffer core assemblies.

In a further or alternative embodiment, the cam of the expanding cam lock is pivotally coupled to the base plate and is configured to slideably engage the follower plate, while in a further or alternative embodiment, the cam includes axle pins pivotally coupling the cam to the base plate. In a further or alternative embodiment, the cam is configured to lock the base plate and follower plate into engagement with the gel cassettes of the buffer core assemblies when the cam is in the second position. In a further or alternative embodiment, the cam includes a push bar configured to engage the base plate to prevent further urging of the first and second surfaces toward the first and second buffer core assemblies. In a further or alternative embodiment, the cam includes a handle to pivot the cam relative to the base plate and follower plate. In a further or alternative embodiment, the cam further has a curved end that slidingly engages the follower plate. In a further or alternative embodiment, the first and second surfaces include push tabs adapted to facilitate urging of the first and second surfaces against the first and second buffer core assemblies. In a further or alternative embodiment, the base plate includes first side panels on a reverse side opposing the first surface and the follower plate includes second side panels on a reverse side opposing the second surface, the first and second side panels being coupled together, while in a still further or alternative embodiment, such a first side panels include slots and the second side panels include lever arms with locking portions configured to slideably engage the slots.

In further or alternative embodiments, the base plate, follower plate, and cam are made of plastic selected from the styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate the expanding cam lock described herein include, but are not limited to epoxy based polymers, cyclo-olefin copolymer (COC), polychlorotrifluoroethylene (PCTFE), polyetheretherketone (PEEK), polyetherimide (PEI), polyethersulfone (PES), polyethylene (PE), high density polyethylene (HDPE), low density polyethylene (LDPE), polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinylfluoride (PVF), polyvinylidenechloride (PVDC), polybutyleneterephthalate (PBT), fluorinated ethylenepropylene (FEP), perfluoroalkoxyalkane (PFA), and polyvinylidenefluoride (PVDF) and copolymers thereof.

In further or alternative embodiments, the base plate, follower plate, and cam are fabricated by molding techniques, hot embossing methods, casting processes, thermoforming methods, stereolithography processes, machining methods and milling processes. In further or alternative embodiments, the base plate, follower plate, and cam are fabricated by injection molding. In further or alternative embodiments, the base plate, follower plate, and cam are fabricated by compression molding. In further or alternative embodiments, the base plate, follower plate, and cam are fabricated by machining.

In another aspect of the expanding cam lock described herein is an expanding cam lock for securing electrophoresis gel cassettes to first and second buffer core assemblies in an electrophoresis container, wherein the container has a first end wall defining a first recess and a second end wall defining a second recess, and the first buffer core assembly is disposed in the container proximate the first end wall and the second buffer core assembly is disposed in the container proximate the second end wall. Also, the expanding cam lock includes a base plate having a first surface adapted to engage the first buffer core assembly and first side panels on the reverse side of the first surface, a follower plate having a second surface adapted to engage the second buffer core assembly and second side panels on the reverse side of the second surface, the first and second side panels being slideably coupled and the base plate and follower plate being configured for insertion between the first and second buffer core assemblies and a cam pivotally coupled to the base plate, the cam slidingly engaging the follower plate to urge the first surface to secure one or more gel cassettes in the first buffer core assembly and the second surface to secure one or more gel cassettes in the second buffer core assembly.

In a further or alternative embodiment, the cam is configured to lock the base plate and the follower plate into engagement with the gel cassettes of the first and second buffer core assemblies. In a further or alternative embodiment, the first side panels of the mounting block include axle bushings. In a further or alternative embodiment, the cam includes axle pins pivotally coupled in the axle bushings. In a further or alternative embodiment, the first side panels include slots and the second side panels include lever arms with locking portions configured to slideably engage with the slots. In a further or alternative embodiment, the cam includes a push bar configured to engage the base plate to prevent further urging of the first and second surfaces toward the first and second buffer core assemblies. In a further or alternative embodiment, the cam includes a handle to pivot the cam relative to the base plate and follower plate. In a further or alternative embodiment, the cam further has a curved end that slidingly engages the follower plate. In a further or alternative embodiment, the first and second surfaces include push tabs adapted to facilitate urging the first and second surfaces against the first and second buffer core assemblies.

Another aspect described herein is a method for securing first and second buffer core assemblies having electrophoresis gel cassettes in an electrophoresis container using the expanding cam described herein. In a further or alternative embodiment, the method involves obtaining a base plate having a first surface adapted to engage the first buffer core assembly and a follower plate having second surface adapted to engage the second buffer core assembly. The follower plate is slideably coupled to the base plate and a cam is positioned between, and moveably coupled with, the base plate and the follower plate. The base plate, the follower plate and the cam are inserted between the first and second buffer core assemblies in the electrophoresis container. The cam is moved from an open position to a closed position to urge the first and second surfaces to secure the gel cassettes to the first and second buffer core assemblies. In a further or alternative embodiment, moving the cam to the closed position causes the cam to lock the base plate and the following plate into engagement with the gel cassettes of the first and second buffer core assemblies.

In another aspect of the expanding cam described herein are electrophoresis kits which include, but are not limited to, an electrophoresis container having a first end wall defining a first recess and a second end wall defining a second recess; at least one buffer core assembly; and an expanding cam lock. The expanding cam of which includes, but is not limited to, a base plate having a first surface adapted to engage a buffer core assembly and having first side panels on the reverse side of the first surface; a follower plate having a second surface adapted to engage a partition assembly and having second side panels on the reverse side of the second surface, the first and second side panels being slideably coupled and the base plate and follower plate being configured for insertion between the first buffer core assembly and the partition assembly; and a cam pivotally coupled to the base plate and the cam slidingly engaging the follower plate.

In further or alternative embodiment, the partition assemblies of such kits are selected from a buffer dam, a buffer displacement dam, or a buffer core assembly comprising at least one electrophoresis gel cassette. In further or alternative embodiment, at least one of the electrophoresis container, the base plate, the follower plate, the cam, the partition assembly or the buffer core assembly is made of a polymer selected from the group consisting of styrene acrylonitrile, polycarbonate, polystyrene, acrylic, acrylate, polymethyl methacrylate, polyethylene, high density polyethylene, polyethylene terephthalate, glycol-modified polyethylene terephthalate, polypropylene, polyoxymethylene, Acetel and copolymers thereof. In further or alternative embodiment, at least one of the electrophoresis container, the base plate, the follower plate, the cam, the partition assembly or the buffer core assembly is fabricated by a molding technique. In further or alternative embodiment, the molding technique is injection molding. In further or alternative embodiment, at least one of the electrophoresis container, the base plate, the follower plate, the cam, the partition assembly or the buffer core assembly is fabricated by machining.

In further or alternative embodiment, the cam includes axle pins pivotally coupling the cam to the base plate. In further or alternative embodiment, the cam is configured to lock the base plate into engagement with the electrophoresis gel cassette of the buffer core and to lock the follower plate into engagement with the partition assembly when the cam is in the second position. In further or alternative embodiment, the cam includes a push bar configured to engage the base plate to prevent further urging of the first surface toward the buffer core assembly and the second surface toward the partition assembly. In further or alternative embodiment, the cam includes a handle to pivot the cam relative to the base plate and follower plate. In further or alternative embodiment, the cam further has a curved end that slidingly engages the follower plate. In further or alternative embodiment, the first and second surfaces include push tabs adapted to facilitate urging of the first surface toward the buffer core assembly and the second surface toward the partition assembly. In further or alternative embodiment, the first side panels include slots and the second side panels include lever arms with locking portions configured to slideably engage the slots.

In another aspect of the expanding cam described herein are electrophoresis assemblies which include an electrophoresis container having a first end wall defining a first recess and a second end wall defining a second recess; a buffer core assembly disposed in the container proximate the first end wall; a partition assembly disposed in the container proximate the second end wall; and an expanding cam lock for sealing at least one electrophoresis gel cassette to the buffer core assembly.

In a further or alternative embodiment, the expanding cam lock includes a base plate having a first surface adapted to engage the buffer core assembly and having first side panels on the reverse side of the first surface; a follower plate having a second surface adapted to engage the partition assembly, and having second side panels on the reverse side of the second surface, the first and second side panels being slideably coupled and the base plate and follower plate being configured for insertion between the buffer core assembly and the partition assembly; and a cam pivotally coupled to the base plate and the cam slidingly engaging the follower plate to urge the second surface toward the partition assembly and to urge the first surface to secure one or more electrophoresis gel cassettes in the first buffer core assembly. In a further or alternative embodiment, the partition assemblies of such electrophoresis assemblies are selected from buffer dam, a buffer displacement dam, or a buffer core assembly comprising at least one electrophoresis gel cassette.

In further or alternative embodiments, at least one of the electrophoresis container, the base plate, the follower plate, the cam, the partition assembly or the buffer core assembly is made of a polymer selected from the group consisting of styrene acrylonitrile, polycarbonate, polystyrene, acrylic, acrylate, polymethyl methacrylate, polyethylene, high density polyethylene, polyethylene terephthalate, glycol-modified polyethylene terephthalate, polypropylene, polyoxymethylene, Acetel and copolymers thereof. In further or alternative embodiments, at least one of the electrophoresis container, the base plate, the follower plate, the cam, the partition assembly or the buffer core assembly is fabricated by a molding technique. In further or alternative embodiments, the molding technique is injection molding. In further or alternative embodiments, at least one of the electrophoresis container, the base plate, the follower plate, the cam, the partition assembly or the buffer core assembly is fabricated by machining.

In a further or alternative embodiment, the cam includes axle pins pivotally coupling the cam to the base plate. In a further or alternative embodiment, the cam is configured to lock the base plate into engagement with the electrophoresis gel cassette of the buffer core and to lock the follower plate into engagement with the partition assembly when the cam is in the second position. In a further or alternative embodiment, the cam includes a push bar configured to engage the base plate to prevent further urging of the first surface toward the buffer core assembly and the second surface toward the partition assembly. In a further or alternative embodiment, the cam includes a handle to pivot the cam relative to the base plate and follower plate. In a further or alternative embodiment, the cam further has a curved end that slidingly engages the follower plate. In a further or alternative embodiment, the first and second surfaces include push tabs adapted to facilitate urging of the first surface toward the buffer core assembly and the second surface toward the partition assembly. In a further or alternative embodiment, the first side panels include slots and the second side panels include lever arms with locking portions configured to slideably engage the slots.

In another aspect described herein is an apparatus for electrophoresis or electrophoretic transfer of biomolecules that comprises a buffer displacement dam in at least one buffer reservoir of the apparatus, wherein the buffer displacement dam conforms to the size of the interior of the buffer reservoir in at least one dimension, and wherein the buffer displacement dam replaces buffer that would otherwise be contained within the buffer reservoir during electrophoretic separation or transfer of biomolecules. In further or alternative embodiments, the buffer displacement dam comprises a bottom and at least three sides. In further or alternative embodiments, the buffer displacement dam comprises a bottom and at least four sides. In further or alternative embodiments, the buffer displacement dam is solid. In further or alternative embodiments, the buffer displacement dam is partially or substantially hollow. In further or alternative embodiments, the at least four sides of the buffer displacement dam define an interior space. In further or alternative embodiments, the buffer displacement dam comprises one or more interior support structures. In further or alternative embodiments, the aid buffer displacement dam replaces a volume of buffer equal to at least 10% of the total volume of the at least one buffer reservoir. In further or alternative embodiments, the buffer displacement dam replaces a volume of buffer equal to at least 20% of the total volume of the at least one buffer reservoir. In further or alternative embodiments, the buffer displacement dam replaces a volume of buffer equal to at least 30% of the total volume of the at least one buffer reservoir. In further or alternative embodiments, the buffer displacement dam resplaces a volume of buffer equal to at least 40% of the total volume of the at least one buffer reservoir.

In further or alternative embodiments, the buffer displacement dam comprises one or more polymers or copolymers selected from the styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate the expanding cam lock described herein include, but are not limited to epoxy based polymers, cyclo-olefin copolymer (COC), polychlorotrifluoroethylene (PCTFE), polyetheretherketone (PEEK), polyetherimide (PEI), polyethersulfone (PES), polyethylene (PE), high density polyethylene (HDPE), low density polyethylene (LDPE), polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinylfluoride (PVF), polyvinylidenechloride (PVDC), polybutyleneterephthalate (PBT), fluorinated ethylenepropylene (FEP), perfluoralkoxyalkane (PFA), and polyvinylidenefluoride (PVDF) and copolymers thereof.

In further or alternative embodiments, the buffer displacement dam may be fabricated by molding techniques, hot embossing methods, casting processes, thermoforming methods, stereolithography processes, machining methods and milling processes. In further or alternative embodiments, the base plate, follower plate, and cam are fabricated by injection molding. In further or alternative embodiments, the buffer displacement dam may be fabricated by compression molding. In a further or alternative embodiment, the buffer displacement dam may be fabricated by machining.

In a further or alternative embodiment, the apparatus is an electrophoretic gel blotting apparatus. In further or alternative embodiments, the electrophoretic gel blotting apparatus includes a buffer reservoir in the form of a buffer tank that includes at least one gel cassette used for electrophoretic transfer of biomolecules. In further or alternative embodiments, the at least one gel cassette is smaller than the maximum size of gel cassette that the electrophoretic gel blotting apparatus can accommodate. In further or alternative embodiments, the gel blotting apparatus is designed to accommodate multiple gel cassettes. In further or alternative embodiments, the electrophoretic gel blotting apparatus comprises fewer than the maximum number of gel cassettes it is designed to accommodate.

In further or alternative embodiments, the apparatus is a gel electrophoresis apparatus. In further or alternative embodiments, the gel electrophoresis apparatus includes at least one gel or gel cassette used for electrophoretic separation of biomolecules. In further or alternative embodiments, the apparatus comprises fewer than the maximum number of gels or gel cassettes it is designed to accommodate. In further or alternative embodiments, the buffer displacement dam replaces the space otherwise occupied by cathode buffer. In further or alternative embodiments, the buffer displacement dam replaces the space otherwise occupied by anode buffer.

In further or alternative embodiments, the apparatus comprises a container designed to accommodate multiple buffer cores. In further or alternative embodiments, the apparatus comprises fewer than the maximum number of buffer cores the container is designed to accommodate. In further or alternative embodiments, the buffer displacement dam occupies a position of the container which is designed to hold a buffer core. In further or alternative embodiments, the buffer displacement dam occupies space designed to hold a buffer core and space in the container designed to hold lower reservoir buffer. In further or alternative embodiments, the container is designed to hold two or more buffer cores, and the container includes at least one buffer core, at least one gel cassette, and a buffer displacement dam.

In further or alternative embodiments, the buffer displacement dam used in an gel electrophoresis apparatus has at least four walls that define an interior space, and the dimensions of the buffer displacement dam conforms to the inner dimension of one end of the container of such an apparatus. In further or alternative embodiments, the buffer displacement dam includes a wall that can be engaged by a cam lock device for sealing at least one gel cassette to a buffer core in such an apparatus. In further or alternative embodiments, the cam lock device is an expanding cam lock device.

In further or alternative embodiments, in a gel electrophoresis apparatus the buffer displacement dam replaces a volume of from about 50 milliliters to about 1,500 milliliters. In further or alternative embodiments, in a gel electrophoresis apparatus the buffer displacement dam replaces a volume of from about 100 milliliters to about 1,500 milliliters. In further or alternative embodiments, in a gel electrophoresis apparatus the buffer displacement dam replaces a volume of from about 200 milliliters to about 1,500 milliliters. In further or alternative embodiments, in a gel electrophoresis apparatus the buffer displacement dam replaces a volume of from about 400 milliliters to about 1,000 milliliters. In further or alternative embodiments, in a gel electrophoresis apparatus the buffer displacement dam replaces a volume of from about 500 milliliters to about 750 milliliters.

In further or alternative embodiments, the gel electrophoresis apparatus is a midi gel apparatus and the buffer displacement dam replaces a volume of from about 50 milliliters to about 1,500 milliliters. In further or alternative embodiments, the gel electrophoresis apparatus is a midi gel apparatus and the buffer displacement dam replaces a volume of from about 100 milliliters to about 1,500 milliliters. In further or alternative embodiments, the gel electrophoresis apparatus is a midi gel apparatus and the buffer displacement dam replaces a volume of from about 200 milliliters to about 1,500 milliliters. In further or alternative embodiments, the gel electrophoresis apparatus is a midi gel apparatus and the buffer displacement dam replaces a volume of from about 400 milliliters to about 1,000 milliliters. In further or alternative embodiments, the gel electrophoresis apparatus is a midi gel apparatus and the buffer displacement dam replaces a volume of from about 500 milliliters to about 750 milliliters.

In further or alternative embodiments, the gel electrophoresis apparatus is an electrophoretic transfer apparatus and the buffer displacement dam replaces a volume of from about 50 milliliters to about 1,500 milliliters. In further or alternative embodiments, the gel electrophoresis apparatus is an electrophoretic transfer apparatus and the buffer displacement dam replaces a volume of from about 100 milliliters to about 1,500 milliliters. In further or alternative embodiments, the gel electrophoresis apparatus is an electrophoretic transfer apparatus and the buffer displacement dam replaces a volume of from about 200 milliliters to about 1,500 milliliters. In further or alternative embodiments, the gel electrophoresis apparatus is an electrophoretic transfer apparatus and the buffer displacement dam replaces a volume of from about 400 milliliters to about 1,000 milliliters. In further or alternative embodiments, the gel electrophoresis apparatus is an electrophoretic transfer apparatus and the buffer displacement dam replaces a volume of from about 500 milliliters to about 750 milliliters.

In further or alternative embodiments, the buffer displacement dam may be used for replacing transfer buffer in an electrophoretic transfer apparatus, in which the buffer displacement dam includes a bottom and at least four walls that define an interior space, and the four walls buffer displacement dam conform to the internal dimensions of at least a portion of the container of the electrophoretic transfer apparatus. In further or alternative embodiments, the buffer displacement dam may be used for replacing electrophoresis buffer in a gel electrophoresis apparatus, in which the buffer displacement dam includes a bottom and at least four walls that define an interior space, and the four walls buffer displacement dam conform to the internal dimensions of at least a portion of a buffer reservoir of the electrophoretic transfer apparatus. In further or alternative embodiments, the buffer displacement dam of such an electrophoresis apparatus includes a buffer tank that can accommodate multiple buffer cores, and the buffer displacement dam conforms to the internal dimensions of the buffer tank, and the buffer displacement dam is designed to occupy the position of at least one of the multiple buffer cores when positioned in the buffer tank. In further or alternative embodiments, the buffer displacement dam, when positioned in the buffer tank, occupies the space in the buffer tank that is designed to hold the second buffer core and space in the buffer tank that holds buffer during use of the apparatus in the absence of the buffer displacement dam.

In further or alternative embodiments, the buffer displacement dam can fit into a midi-gel apparatus container. In further or alternative embodiments, the buffer displacement dam is from about 3 to about 30 inches in height. In further or alternative embodiments, the buffer displacement dam is from about 3 to about 20 inches in height. In further or alternative embodiments, the buffer displacement dam is from about 3 to about 10 inches in height. In further or alternative embodiments, the buffer displacement dam is from about 3 to about 6 inches in height. In further or alternative embodiments, the buffer displacement is from about 3.5 to about 5 inches in height. In further or alternative embodiments, the buffer displacement dam is about 4.5 inches in height. In further or alternative embodiments, the buffer displacement dam is from about 4 to about 40 inches in length. In further or alternative embodiments, the buffer displacement dam is from about 4 to about 30 inches in length. In further or alternative embodiments, the buffer displacement dam is from about 4 to about 20 inches in length. In further or alternative embodiments, the buffer displacement dam is from about 4 to about 10 inches in length. In further or alternative embodiments, the buffer displacement dam is from about 4 to about 8 inches in length. In further or alternative embodiments, the buffer displacement dam is about 6.14 inches in length. In further or alternative embodiments, the buffer displacement dam is from about 1 to about 25 inches in width. In further or alternative embodiments, the buffer displacement dam is from about 1 to about 20 inches in width. In further or alternative embodiments, the buffer displacement dam is from about 1 to about 15 inches in width. In further or alternative embodiments, the buffer displacement dam is from about 1 to about 10 inches in width. In further or alternative embodiments, the buffer displacement dam is from about 1 to about 5 inches in width. In further or alternative embodiments, the buffer displacement dam is from about 1 to about 3 inches in width. In further or alternative embodiments, the buffer displacement dam is about 1.66 inches in width. In further or alternative embodiments, the buffer displacement dam has a lip on one end.

In another aspect described herein are methods for performing electrophoretic transfer of one or more biomolecules from a gel to a filter or membrane, wherein such methods include positioning within a buffer tank a gel cassette comprising a transfer membrane and a gel that comprises one or more biomolecules, wherein the buffer tank comprises or contacts two electrodes; adding a buffer displacement dam to the buffer tank; adding transfer buffer to the buffer tank; connecting a power source to the two electrodes; and applying a voltage across the gel to cause electrophoretic transfer of the one or more biomolecules from the gel to the transfer membrane.

In another aspect described herein are methods for performing electrophoretic separation of one or more biomolecules, wherein such methods include positioning at least one gel cassette in a gel electrophoresis apparatus such that one end of a gel enclosed within the gel cassette is in contact with a first buffer reservoir and another end of the gel enclosed within the gel cassette is in contact with a second buffer reservoir, wherein the first buffer reservoir comprises or contacts a first electrode and the second buffer reservoir comprises or contacts a second electrode; adding a buffer displacement dam to the f gel electrophoresis apparatus; adding electrophoresis buffer to the first buffer reservoir and the second reservoir; adding one or more samples comprising one or more biomolecules to sample wells at one end of the gel; connecting the first electrode and the second electrode to a power source; and applying a voltage across the gel to separate one or more biomolecules.

In another aspect described herein is a buffer displacement dam for replacing electrophoresis buffer in an electrophoretic apparatus having a tank, an anode reservoir, and a cathode reservoir, wherein the buffer dam comprises non-conductive material and is positioned within a tank of the biological research apparatus in a position otherwise occupied by a buffer core, such that less than 90% of the buffer is necessary within either the anode reservoir or the cathode reservoir compared to the amount of buffer required in the absence of the buffer displacement dam. In further or alternative embodiments, the electrophoretic apparatus is a gel electrophoresis apparatus. In further or alternative embodiments, the electrophoretic is a gel blotting apparatus. In further or alternative embodiments, wherein less than 75% of the buffer is required than is necessary in the absence of the buffer displacement dam. In further or alternative embodiments, wherein less than 50% of the buffer is required than is necessary in the absence of the buffer displacement dam. In further or alternative embodiments, wherein less than 25% of the buffer is required than is necessary in the absence of the buffer displacement dam. In further or alternative embodiments, wherein less than 5% of the buffer is required than is necessary in the absence of the buffer displacement dam.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
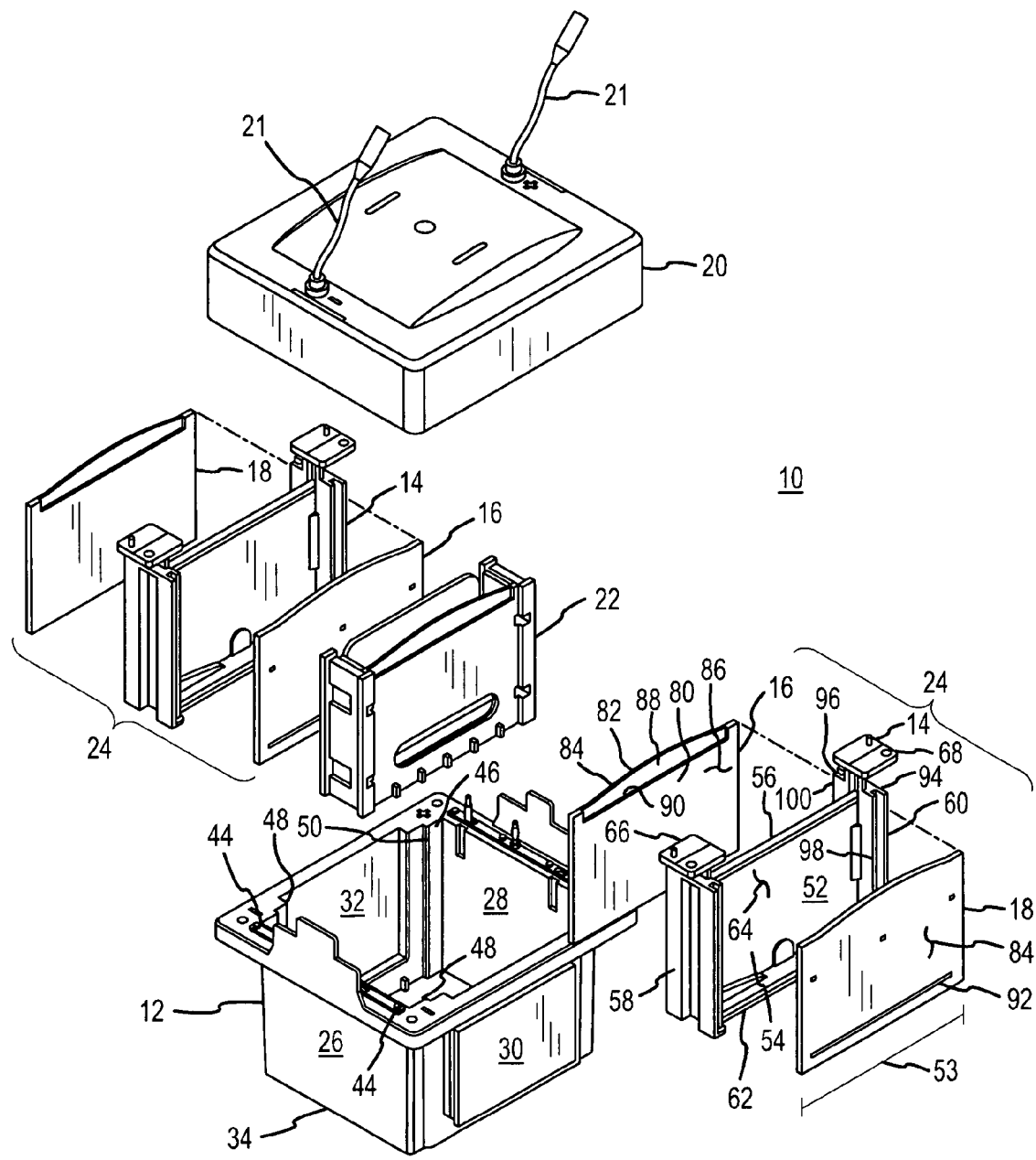
FIG. 1 is an exploded perspective view of an electrophoresis cell assembly that includes an expanding cam lock configured in accordance with an example embodiment of the invention.

Unless otherwise defined, all technical and scientific terms used herein have the meaning commonly understood by one skilled in the biotechnology art. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description. The following detailed descriptions are merely illustrative in nature and is not intended to limit the invention or the application and uses of the invention. Furthermore, there is no intention to be bound by any expressed or implied theory presented in the preceding technical field, background, brief summary or the following detailed descriptions.

Expanding Cam Lock

The expanding cam lock described herein may be used in various electrophoresis apparatuses, including but not limited to gel electrophoresis apparatuses, to secure and/or seal at least one electrophoresis gel cassette within the electrophoresis apparatus. The expanding cam lock comprises i) a base plate having a first surface adapted to engage either a partition assembly or a buffer core assembly which includes at least one electrophoresis gel cassette; ii) a follower plate having a second surface adapted to engage either a partition assembly or a buffer core assembly which includes at least one electrophoresis gel cassette; and iii) a cam positioned between and moveably coupled with the base plate and the follower plate. The base plate and the follower plate are slideably coupled together and configured for insertion between the buffer core assemblies or the partition assembly and buffer core assembly in the electrophoresis apparatus. The cam may also be pivotally coupled to the base plate and may be configured to slideably engage the follower plate. The cam is movable from a first position to a second position which urges or otherwise moves the base plate and the follower plate toward either a buffer core assembly or a partition assembly, depending on the configuration used with the expanding cam lock. The first surface of the base plate and the second surface of the follower plate will contact either an electrophoresis gel cassette of a buffer core assembly or a partition assembly, and thereby sealing the electrophoresis gel cassette to the buffer core assembly. By way of example only, the following configurations may be used, i) the base plate may move toward and the first surface of the base plate may contact an electrophoresis gel cassette of a buffer core assembly, while the follower plate may move toward and the second surface of the follower plate may contact a partition assembly;

ii) the base plate may move toward and the first surface of the base plate may contact a partition assembly, while the follower plate may move toward and the second surface of the follower plate may contact an electrophoresis gel cassette of a buffer core assembly;

iii) the base plate may move toward and the first surface of the base plate may contact an electrophoresis gel cassette of a buffer core assembly, while the follower plate may move toward and the second surface of the follower plate may contact a different electrophoresis gel cassette of a different buffer core assembly; or iv) the base plate may move toward and the first surface of the base plate may contact a partition assembly, while the follower plate may move toward and the second surface of the follower plate may contact a partition assembly.

The electrophoresis apparatus, in which the expanding cam lock is used, includes a container wherein the expanding cam lock, buffer core assembly or buffer core assemblies, electrophoresis gel cassette(s), and partition assembly are placed. The partition assembly is either a buffer core assembly comprising at least one electrophoresis gel cassette, or the partition assembly is an object which may be used to partition or block out the electrophoresis container into smaller volume increments. Such objects include, but are not limited to, a buffer dam and a buffer displacement dam.

As used herein a buffer dam is a barrier which blocks the access of buffer from one region of the container into another region of the container, thereby partitioning the container. By way of example only, such a buffer dam may resemble a buffer core wherein a wall is present instead of a gel cassette. Alternatively, such a buffer dam may be a simple wall, plate, wedge, or shim which is inserted into the container and becomes a barrier to block buffer flow or redistribution.

As used herein a buffer displacement dam is a barrier which blocks the access of buffer from one region of the container into another region of the container, thereby partitioning the container. A buffer displacement dam is an object which is placed into an electrophoresis container and occupies the space in the container which would otherwise be taken up by buffer. A buffer displacement dam serves to occupy the space which would otherwise be occupied by buffer, while a buffer dam blocks the buffer from moving into empty regions.

The expanding cam lock described herein may be used in an electrophoresis apparatus to secure and/or seal multiple buffer cores and each buffer core may include multiple electrophoresis gel cassettes. By way of example only, the expanding cam lock may be used to secure and/or seal 1, 2, 3, 4, 5, 6, 7, 8, 9, 10, 11, 12, 13, 14, 15, 16, 17, 18, 19, 20, 21, 22, 23, or 24 buffer cores with 1, 2, 3, 4, 5, 6, 7, 8, 9, 10, 11, 12, 13, 14, 15, 16, 17, 18, 19, 20, 21, 22, 23, or 24 gel cassettes per buffer core. In addition, multiple expanding cams may be used per electrophoresis apparatus. By way of example only, the number of expanding cam locks which may be used in an electrophoresis apparatus may be 1, 2, 3, 4, 5, 6, 7, 8, 9, 10, 11, 12, 13, 14, 15, 16, 17, 18, 19, 20, 21, 22, 23, or 24.

An exploded perspective view of an electrophoresis system 10 including an exemplary embodiment of the present invention is shown in FIG. 1. The system 10 includes a container 12, a lid 20, an expanding cam lock 22, and first and second buffer core assemblies 24. Each buffer core assembly 24 includes a buffer core body 14 and gel cassettes 16 and 18.

Container 12 includes side walls 26 and 28, end walls 30 and 32, and a closed bottom 34. Container 12 is open at the top for receiving a first electrophoresis buffer solution (not shown). Located on opposite inner surfaces of side walls 26 and 28 and spaced away from the end walls 30 and 32 of container 12 are wall recesses 44 and 46. Wall recesses 44 and 46 are aligned with each other to receive each buffer core assembly 24 and are integrally formed with side walls 26 and 28, respectively. Each of the wall recesses 44 and 46 has a cross-section resembling an irregular C-channel when viewed from the top of container 12.

Wall recesses 44 and 46 are sized to accommodate the lateral width 53 of buffer core assembly 24 without significant lateral movement. The width of wall recesses 44 and 46 is slightly greater than width 53 to facilitate the placement of each buffer core assembly 24 in container 12.

Container 12 also features vertical ridges 48 and 50. Vertical ridges 48 and 50 extend along the height of container 12 where wall recesses 44 and 46 open to side walls 26 and 28 toward end walls 30 and 32 of container 12. Vertical ridges 48 and 50 abut each buffer core assembly 24 in its installed position, as will be discussed in further detail below.

Each buffer core assembly 24 includes gel cassettes 16 and 18, which are placed on a front side 54 and a back side 56 of buffer core body 14 to form a portion of the sides of an upper buffer chamber 52. Upper buffer chamber 52 is liquid-tight and holds a second electrically chargeable buffer solution. In practice, upper buffer chamber 52 often is referred to as the anode chamber or the cathode chamber, depending on the polarity of the applied voltage or applied current to the buffer solution contained in upper buffer chamber 52.

Buffer core body 14 is generally U-shaped, and includes spaced-apart upraised side members 58 and 60, a base 62 and a beam 64. Beam 64 provides support for and connects side members 58 and 60, and is positioned approximately halfway between the front and back sides of buffer core body 14. Flanges 66 and 68 are located at the top portions of side members 58 and 60, respectively.

Gel cassettes 16 and 18 are positioned on each of the front side 54 and back side 56 of buffer core body 14 in a sandwiched fashion. Gel cassettes 16 and 18 have a front surface 80 and a back surface 82. Each gel cassette includes a pair of thin wall plates that are commonly referred to as the divider or divider plate 84 and the retainer or retainer plate 86. Retainer plate 86 is slightly shorter in height than divider plate 84.

Divider plate 84 is affixed to a peripheral ridge (not shown) along the lateral sides and the bottom periphery of retainer plate 86 to define an internal gel compartment 88 for holding an electrophoresis gel (not shown). Gel compartment 88 has a comb opening 90 at the top portion of the cassette for receiving a sample that is to be electrophoretically separated. Located along the lower portion of divider plate 84 and traversing the width of each of gel cassettes 16 and 18 is an opening 92 that opens gel compartment 88 to the exterior of the cassette.

Various electrophoresis gel cassettes, also herein referred to gel cassettes, may be used in conjunction with the expanding cam lock described herein. By way of example only, in typical applications, the gel cassette has a height and width between 4 inches (10 cm) and 8 inches (20 cm). Although gel cassettes are available in various shapes, sizes, and widths (such as mini-gel cassettes, wide-format gel cassettes, or full size gel cassettes), the invention is not limited to any specific size of gel cassette. In addition, by way of example only, a gel cassette may have the gel pre-filled within the internal gel compartment for ease of handling. The comb opening 90 is closed with a comb (not shown) and opening 92 is masked closed with a removable tape (not shown). An example of the gel cassettes which may be used in conjunction with the expanding cam lock described herein are the Tris-glycine gels sold by Invitrogen Corporation, of San Diego, Calif., Catalog No. EC6005. Gel cassettes of similar types are also commercially available from other sources.

Gel cassettes 16 and 18 are positioned adjacent each of front side 54 and back side 56 of buffer core body 14 in a sandwiched fashion to define upper buffer chamber 52 for receiving the second buffer solution (not shown). As will be described in more detail below, the second buffer solution is isolated from the first buffer solution in container 12. In view of the isolation of the two buffer solutions, the portion of container 12 that contains the first buffer solution is often referred to as the lower buffer chamber, as distinguished from upper buffer chamber 52.

Both the front and rear surfaces of buffer core body 14 are provided with grooves 94 and 96 for fitting and holding resilient strips 98 and 100, respectively, as a seal between gel cassettes 16 and 18 and buffer core body 14. The seal ensures isolation of the second buffer solution in upper buffer chamber 52 from the first buffer solution in container 12, and provides a cushion to reduce excess stress along the force bearing surfaces of the cassettes when they are held against buffer core body 14.

Prior to using gel cassettes 16 and 18, the comb (not shown) and the tape (not shown) are removed. The sample to be analyzed is introduced into gel compartment 88 through comb opening 90 by appropriate means, such as a pipette. Each buffer core assembly 24 is then slidably inserted into wall recesses 44 and 46 from the top of the container 12 to rest on risers 104 (see FIG. 5) inside container 12. Risers 104 elevate buffer core assemblies 24 to permit the first buffer solution to pass below and surround the front and back sides of buffer core assemblies 24. Buffer core assemblies 24 are positioned toward end walls 30 and 32 of container 12 such that side ridges 102 of gel cassette 18 are aligned coincidentally with and bear upon vertical ridges 48 and 50.

Although the above description refers to the use of two gel cassettes as part of each buffer core assembly 24, the present invention may also be used with more or less than two cassettes in each buffer core assembly 24. For example, a single cassette can be installed on one side of buffer core body 14, and a blank or a plate member can be placed on the other side to achieve similar performance and results with assured consistency and uniformity.

Figure 2:
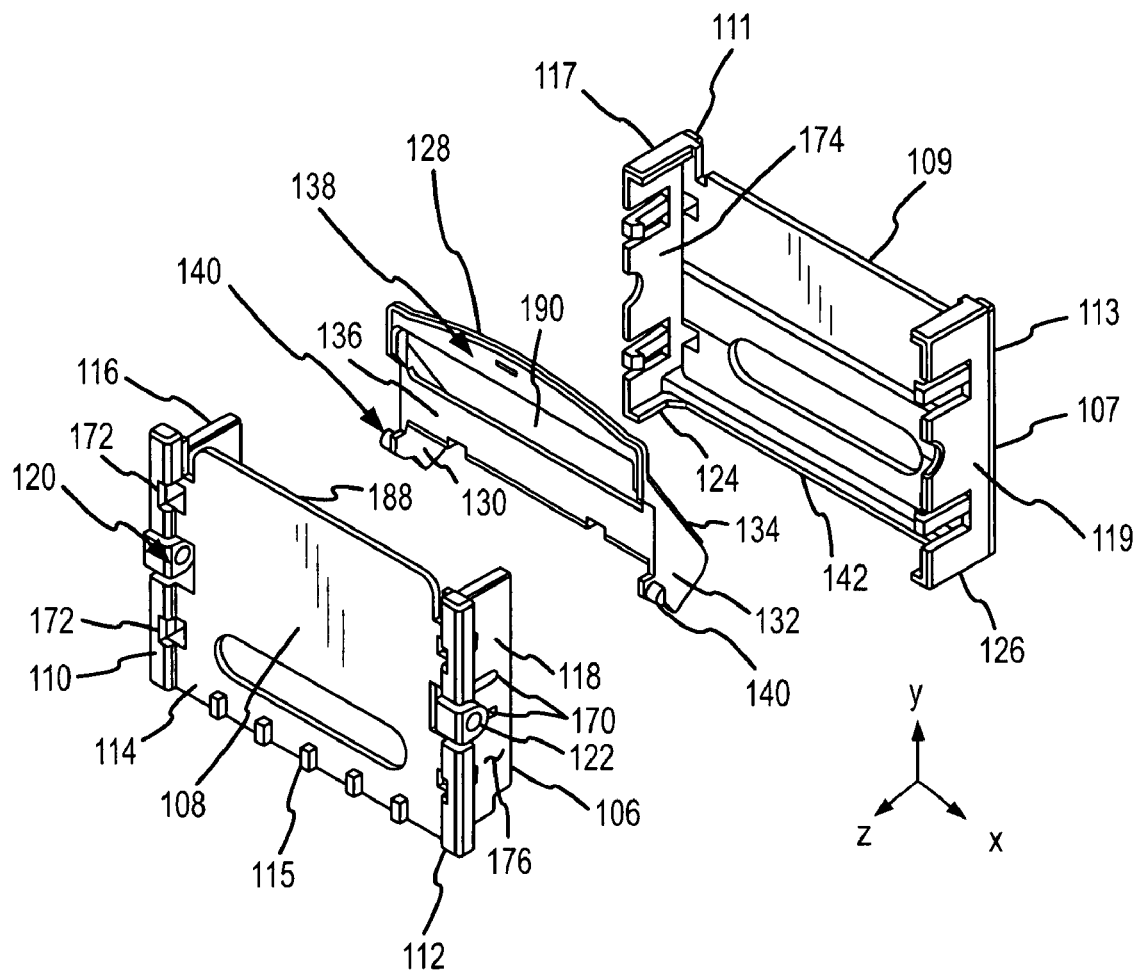
FIG. 2 is an exploded perspective view of the expanding cam lock shown in FIG. 1.

FIG. 2 is an exploded perspective view of expanding cam lock 22, which is used to secure buffer core assemblies 24 in container 12. Expanding cam lock 22 comprises three basic parts: a base plate 106; a follower plate 107; and cam 128.

Base plate 106 includes a generally square or rectangular front panel 108 and contact surfaces 110 and 112 on the lateral sides of front panel 108. At the lower portion of base 114 of front panel 108, a plurality of upraised push tabs 115 are provided to bear upon the bottom edge of divider plate 84 (shown in FIG. 1). Affixed to the reverse side of front panel 108, a pair of spaced apart parallel side panels 116 and 118 is provided to enhance structural integrity of base plate 106 and to couple with side panels 117 and 119 on follower plate 107. Side panels 116 and 118 substantially align with contact surfaces 110 and 112, respectively and include axle bushings 120 and 122. Each side panel 116 and 118 may include one or more slots 170 for coupling with follower plate 107 and front panel 108 may include one or more through holes 172 adjacent the slots.

Follower plate 107 is generally similar to base plate 106 and includes a generally square or rectangular front panel 109 and contact surfaces 111 and 113. At a lower portion of base of front panel 109, a plurality of upraised push tabs are provided (not shown but similar to push tabs 115) to bear upon the bottom edge of divider plate 84. Affixed to the reverse side of front panel 109, a pair of spaced apart parallel side panels 117 and 119 is provided to enhance structural integrity of follower plate 107. Side panels 117 and 119 substantially align with contact surfaces 111 and 115, respectively. Bases 124 and 126 of side panels 117 and 119 extend from the back surface 142 of front panel 108. An inner surface 174 of side panels 117 and 119 is configured to slide against an outer surface 176 of side panels 116 and 118 of the base plate 106. Side panels 117 and 119 also include one or more lever arms 176 with locking ends 178 (see FIG. 3). Slots 170 are configured and sized to accept lever arms 176 and locking ends 178 to slideably couple the base plate 106 and the follower plate 107. The locking ends 178 may also include an angled end portion to facilitate assembly.

Figure 3:
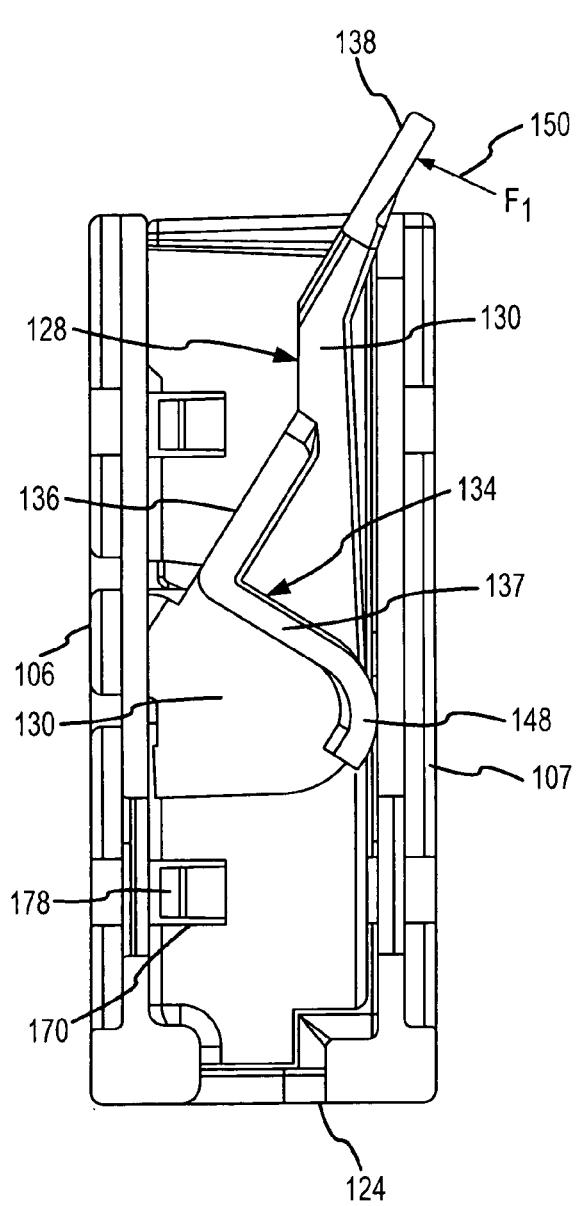
FIG. 3 is a vertical sectional view of an assembled expanding cam lock in the retracted position.

Cam 128 includes cam arms 130 and 132, a push bar 134, a grip or handle 138 and axle pins 140 and 141. Axle pins 140 and 141 extend through and freely pivot in axle bushings 120 and 122 of side panels 116 and 118. As shown in FIG. 3, push bar 134 extends between cam arms 130 and 132 and includes plates 136 and 137, and curved end 148. Referring again to FIG. 2, grip 138 is used to pivot cam 128 relative to base plate 106 and follower plate 107. A recess or opening 190 in cam 128 provides clearance for a top portion 188 of front panel 108 when expanding cam lock 22 is in the expanded position (shown in FIG. 4). The length of handle 138 is longer than push bar 134, hence the force that is applied to handle 138 is multiplied by the ratio of lengths of handle 138 and push bar 134. The mechanical advantage results in the force applied by push bar 134 being greater than the force applied by the user to handle 138. This allows higher sealing forces to be applied by the user.

The expanding cam lock described herein, including base plate 106, follower plate 107 and cam 128, may be fabricated from a number of materials including, but not limited to polymeric materials. Such polymers include, but not limited to, styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate the expanding cam lock described herein include, but are not limited to epoxy based polymers, cyclo-olefin copolymer (COC), polychlorotrifluoroethylene (PCTFE), polyetheretherketone (PEEK), polyetherimide (PEI), polyethersulfone (PES), polyethylene (PE), high density polyethylene (HDPE), low density polyethylene (LDPE), polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinylfluoride (PVF), polyvinylidenechloride (PVDC), polybutyleneterephthalate (PBT), fluorinated ethylenepropylene (FEP), perfluoralkoxy-alkane (PFA), and polyvinylidenefluoride (PVDF).

The expanding cam lock described herein, including base plate 106, follower plate 107 and cam 128, can be fabricated using a variety of techniques, processes and methods. Such techniques, processes and methods include, but are not limited to, molding techniques, hot embossing methods, casting processes, thermoforming methods, stereolithography processes, machining methods and milling processes. Such molding techniques include, but are not limited to, injection molded and compression molding. In the embodiments described herein, and by way of example only, The expanding cam lock described herein, including base plate 106, follower plate 107 and cam 128, may be formed by injection molding a plastic material, such as SAN (styrene acrylonitrile), Polycarbonate, Polystyrene, Acrylic, PMMA (polymethyl methacrylate), PET, PETG, or Polypropylene. Alternatively, the expanding cam lock described herein, including base plate 106, follower plate 107 and cam 128, may be machined from polyoxymethylene copolymer, such as Acetel, or formed from high strength epoxies using a stereolithograpy processes.

Expanding cam lock 22 is assembled by first positioning cam 128 within side panels 116 and 118 of base plate 106 and inserting axle pins 140 and 141 into axle bushings 120 and 122. Axle pins 140 and 141 and/or axle bushings 120 and 122 should have enough flexibility to allow flexing, entry and retention of axle pins 140 and 141 in axle bushings 120 and 122. Follower plate 107 is then positioned such that inner surface 174 of side panels 117 and 119 engages outer surface 176 of side panels 116 and 118 of base plate 106. The angled ends of locking ends 178 flex lever arms 176 until locking ends 178 slide along side panels 116 and 118 and drop into slots 170, slideably locking base plate 106 and follower 107 plate together with cam 128 sandwiched between. Follower plate 107 may be removed by flexing lever arms 176 until locking ends 178 are out of slots 170 and then sliding follower plate 107 away from base plate 106.

When assembled, cam 128 rotates around the X-axis through axle pins 140 and 141. In the preferred embodiment, cam 128 cannot translate relative to base plate 106 in the X, Y or Z directions, and base plate 106 and follower plate 107 are slideably locked together such that they cannot rotate relative to each other. Slots 170 are elongated to allow locking ends 178 of lever arms 176 to move within slots 170 and allow base plate 106 and follower plate 107 to translate (slide) along the Z direction.

Figure 4:
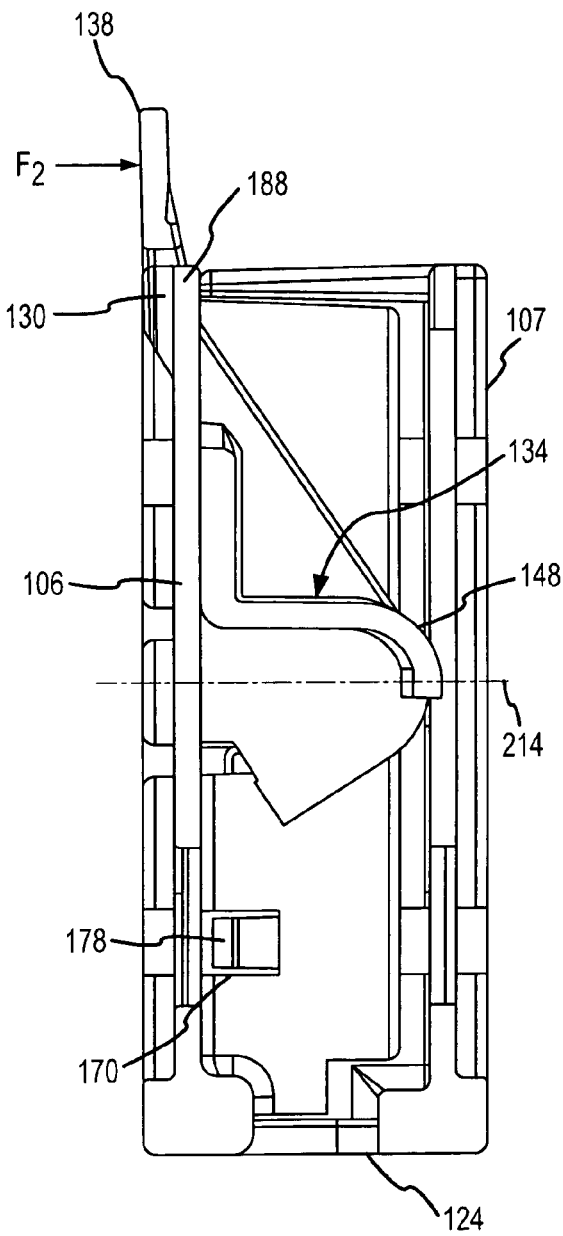
FIG. 4 is a vertical sectional view of an assembled expanding cam lock in the expanded position.

FIGS. 3 and 4 are vertical cross-sectional views showing cam 128 in the open position (FIG. 3) and the closed position (FIG. 4). As a force $F_1$ 150 is applied to handle 138, cam 128 rotates around it's axle pins 140 and 141. During rotation, push bar 134 rotates upward and begins to push follower plate 107 out of its path of rotation. This continues until curved end 148 of push bar 134 passes the orthogonal (90 degree) point at which point it becomes "over-center". The invention makes use of this over-center attribute by stopping the rotation just a few degrees past 90 degrees. In this position, cam 128 exerts outward forces on base plate 106 and follower plate 107, which in turn exerts forces on the seals and cassettes to keep them in place within the container. Note that cam 128 is prevented from over-rotating by the hard stops. Hence, it is compelled to stay in this expanded position until the user applies an opposite force $F_2$ 152 to handle 138 which is greater and overrides the inherent locking force.

Figure 5:
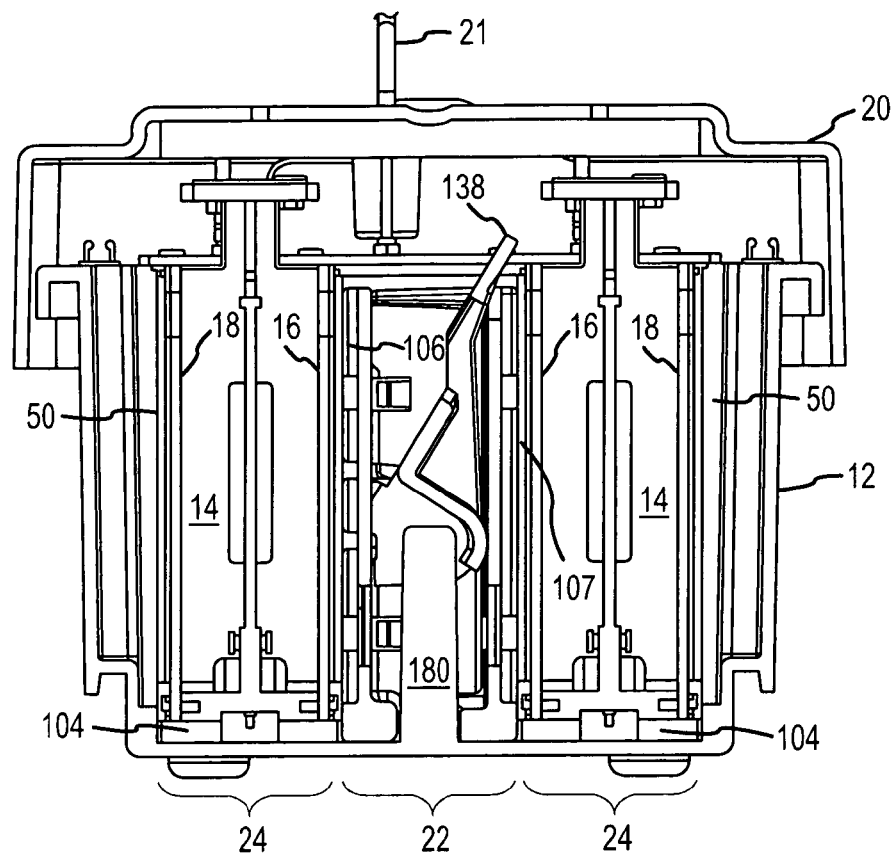
FIG. 5 is a phantom side view of an electrophoresis cell assembly that includes an expanding cam lock in the retracted position.

FIG. 5 is a phantom side view that illustrates expanding cam lock 22 inserted into container 12 with cam 128 disposed in an open position with handle 138 toward the right of container 12. On insertion, base plate 106 is disposed adjacent gel cassette 16 of a first buffer core assembly 24 and follower plate 107 is disposed adjacent a gel cassette 16 of a second buffer core assembly 24. Expanding cam lock 22 includes a central opening in the bottom portion to allow expanding cam lock 22 to straddle a protrusion 180 on the bottom of container 12. As shown in FIG. 5, upon initial insertion into container 12, base plate 106 and follower plate 107 are essentially parallel to each other and also to gel cassettes 16.

Figure 6:
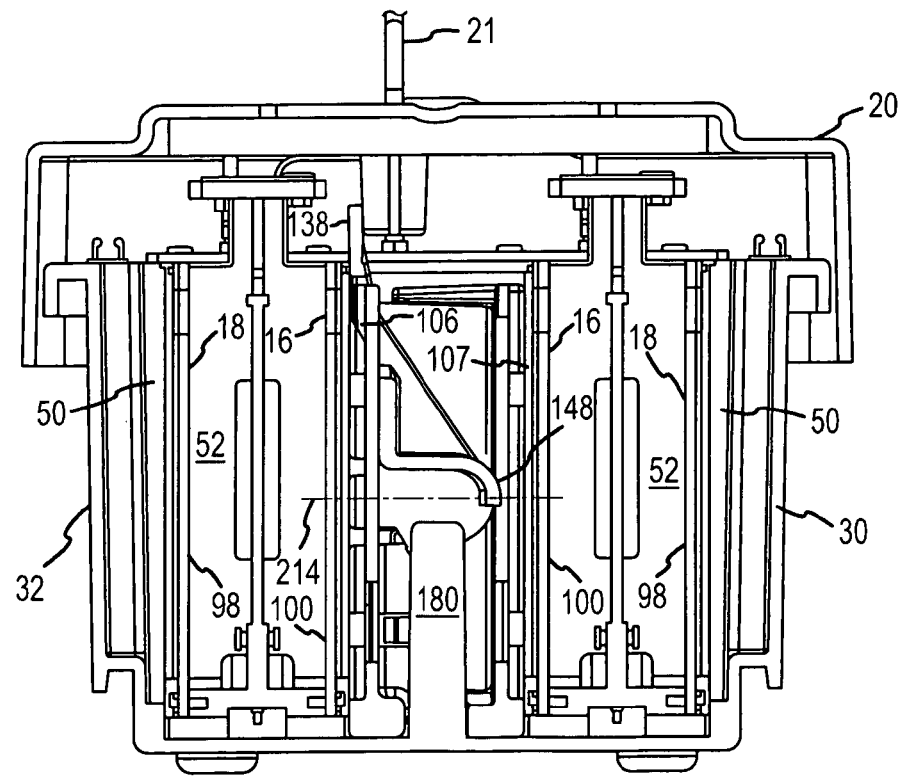
FIG. 6 is a phantom side view of an electrophoresis cell assembly that includes an expanding cam lock in the expanded position.

FIG. 6 illustrates expanding cam lock 22 with cam 128 in a closed position. In particular, cam 128 is shown rotated toward the left of container 12. As cam 128 is rotated left, curved end 148 bears against wall 109 of the follower plate 107, causing the base plate 106 and follower plate 107 to separate. As a result, contact surfaces 110 and 112 of base plate 106 and contact surfaces 111 and 113 of follower plate 107 align with and bear upon the gel cassettes 16, pressing gel cassettes 16 against buffer core bodies 14. Buffer core bodies 14 in turn bear upon gel cassettes 18, pressing gel cassettes 18 against vertical ridges 48 (not shown) and 50. As cam 128 is further rotated forward, curved end 148 passes through a plane extending perpendicularly from wall 32 to the center of axle pins 140 and 141 (shown as dashed line 214 in FIGS. 4 and 6). Cam 128 therefore goes "over-center" at a point where curved end 148 exceeds the point of maximum pressure against follower plate 107, thus locking the expanding cam lock 22 in position. Because force would be required to return cam 128 backward past over-center (i.e., returning curved end 148 below dashed line 214), the over-center position of cam 128 secures base plate 106 and follower plate 107 against gel cassettes 16. Upon further forward motion of cam 128, flat plate 136 of cam 128 contacts the back surface of front panel 108, providing a positive stop that prevents cam 128 from further forward movement.

As contact surfaces 110 and 112 of base plate 106 and contact surfaces 111 and 113 of follower plate 107 bear on side portions of gel cassettes 16, a bearing force is transmitted through gel cassettes 16 and 18 against resilient strips 100 and 98, respectively on each buffer core body 14 to seal upper buffer chambers 52. This ensures fluid and electrical isolation between the first and second buffer solutions in container 12 and in upper buffer chamber 52 to prevent mixing of the two buffer solutions, which can interfere with proper molecular separation. It also reduces the risks of electrical grounding of the power supply or other sensitive instruments used in connection with the electrophoresis. The resiliency of the strips 98 and 100 also provides a means of resistance against the bearing force of base plate 106 and follower plate 107 such that a static balance is maintained among buffer core bodies 14, gel cassettes 16 and 18, base plate 106, follower plate 107, cam 128 and end walls 30 and 32 of container 12, thereby securing them in container 12.

Cam 22 provides a consistent and reproducible clamping force on buffer core assemblies 24. In particular, because cam 128 is pivotally coupled to base plate 106, base plate 106 cannot slip relative to cam 128, and thereby inadvertently release pressure on buffer core assemblies 24. Further, once the curved end 148 goes "over center," cam 22 is locked in position and applies a consistent and reproducible clamping force to buffer core assemblies 24 that does not depend upon the amount of force applied to handle 138.

During operation of the expanding cam described herein, the first and second buffer core assemblies 24 and expanding cam lock 22 are first secured within container 12 in the manner as described above. A first buffer solution is dispensed into each upper buffer chamber 52 above comb openings 90 of gel cassettes 16 and 18 to establish fluid contact with the gel in the gel compartments. A second buffer solution is then introduced into container 12 until its level is approximately that of beam 64. Lid 20 is then positioned above the front portion of container 12, the conductor cables 21 are attached to a power supply system or charging means (not shown) and electrophoresis commences.

Electrophoresis Kit with an Expanding Cam Lock

The expanding cam lock described herein may be incorporated into an electrophoresis kit. Such kits may include, among other components, an electrophoresis container having a first end wall defining a first recess and a second end wall defining a second recess; at least one buffer core assembly, a partition assembly, and an expanding cam lock. The expanding cam lock incorporated into such kits comprises a base plate having a first surface adapted to engage a buffer core assembly and having first side panels on the reverse side of the first surface; a follower plate having a second surface adapted to engage a partition assembly and having second side panels on the reverse side of the second surface, the first and second side panels being slideably coupled and the base plate and follower plate being configured for insertion between the buffer core assembly and the partition assembly; and a cam pivotally coupled to the base plate and the cam slidingly engaging the follower plate. The partition assembly of such kits, have been described herein, and include but are not limited, buffer dams, a buffer displacement dams, or buffer core assemblies comprising at least one electrophoresis gel cassette.

The cam of the expanding cam lock incorporated into an electrophoresis kit may also include axle pins which pivotally couple the cam to the base plate. In addition, the cam may be movable from a first position to a second position which urges or otherwise moves the base plate and the follower plate toward either a buffer core assembly or a partition assembly, depending on the configuration used with the expanding cam lock. The first surface of the base plate and the second surface of the follower plate will contact either an electrophoresis gel cassette of a buffer core assembly or a partition assembly, and thereby sealing the electrophoresis gel cassette to the buffer core assembly. By way of example only, the following configurations may be used, i) the base plate may move toward and the first surface of the base plate may contact an electrophoresis gel cassette of a buffer core assembly, while the follower plate may move toward and the second surface of the follower plate may contact a partition assembly;

ii) the base plate may move toward and the first surface of the base plate may contact a partition assembly, while the follower plate may move toward and the second surface of the follower plate may contact an electrophoresis gel cassette of a buffer core assembly;

iii) the base plate may move toward and the first surface of the base plate may contact an electrophoresis gel cassette of a buffer core assembly, while the follower plate may move toward and the second surface of the follower plate may contact a different electrophoresis gel cassette of a different buffer core assembly; or iv) the base plate may move toward and the first surface of the base plate may contact a partition assembly, while the follower plate may move toward and the second surface of the follower plate may contact a partition assembly.

Additionally, the first surface of the base plate and second surface of the follower plate may include push tabs adapted to facilitate urging of the first surface and the second surface. Also, the first side panels may include slots and the second side panels may include lever arms with locking portions configured to slideably engage the slots.

When the cam is in the second position, the cam may be configured to lock the base plate into engagement with either a partition assembly or an electrophoresis gel cassette of the buffer core and to lock the follower plate into engagement with either a partition assembly or an electrophoresis gel cassette of the buffer core.

The cam of the expanding cam lock incorporated into an electrophoresis kit may also include i) at least one push bar configured to engage the base plate to prevent further urging of the first surface toward the buffer core assembly and the second surface toward the partition assembly; ii) at least one handle to pivot the cam relative to the base plate and follower plate; and/or iii) a curved end that slidingly engages the follower plate.

The components of such electrophoresis kits, including but not limited to, the electrophoresis container, the base plate, the follower plate, the cam, the partition assembly or the buffer core assembly may be made of various materials, such as polymers, metals, or combinations thereof. The polymer used may be selected from the group consisting of styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate these components include, but are not limited to epoxy based polymers, cyclo-olefin copolymer (COC), polychlorotrifluoroethylene (PCTFE), polyetheretherketone (PEEK), polyetherimide (PEI), polyethersulfone (PES), polyethylene (PE), high density polyethylene (HDPE), low density polyethylene (LDPE), , polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinylfluoride (PVF), polyvinylidenechloride (PVDC), polybutyleneterephthalate (PBT), fluorinated ethylenepropylene (FEP), perfluoralkoxyalkane (PFA), and polyvinylidenefluoride (PVDF).

In addition, the components of such electrophoresis kits, including but not limited to, the electrophoresis container, the base plate, the follower plate, the cam, the partition assembly or the buffer core assembly may be fabricated by molding techniques, hot embossing methods, casting processes, thermoforming methods, stereolithography processes, machining methods and milling processes. Such molding methods include, but are not limited to, injection molding and compression molding.

Electrophoresis Assembly with an Expanding Cam Lock

The expanding cam lock described herein may be incorporated into an electrophoresis assembly for sealing at least one electrophoresis gel cassette to a buffer core assembly in the electrophoresis assembly. The components of such assemblies include, but are not limited to an electrophoresis container having a first end wall defining a first recess and a second end wall defining a second recess; a buffer core assembly with at least one gel cassette or a partition assembly disposed in the container proximate the first end wall; a different buffer core assembly with at least one gel cassette or a different partition assembly disposed in the container proximate the second end wall; and an expanding cam lock for sealing at least one electrophoresis gel cassette to a buffer core assembly.

The expanding cam lock of such electrophoresis assemblies include a base plate having a first surface adapted to engage either a partition assembly or a buffer core assembly with at least one gel cassette and the base plate has first side panels on the reverse side of the first surface; a follower plate having a second surface adapted to engage either a partition assembly a buffer core assembly with at least one gel cassette, and the follower plate has second side panels on the reverse side of the second surface, the first and second side panels are slideably coupled and the base plate and follower plate being configured for insertion between the buffer core assemblies, partition assembly or combinations thereof; and a cam pivotally coupled to the base plate and the cam slidingly engaging the follower plate to urge the second surface toward either a partition assembly or a buffer core assembly and to urge the first surface either a different partition assembly or a different buffer core assembly, thereby securing and/or sealing one or more electrophoresis gel cassettes in the buffer core assemblies.

The partition assembly of such electrophoresis assemblies have been described herein, and include but are not limited, buffer dams, a buffer displacement dams, or buffer core assemblies comprising at least one electrophoresis gel cassette.

The cam of the expanding cam lock incorporated into an electrophoresis assemblies may also include axle pins which pivotally couple the cam to the base plate. In addition, the cam may be movable from a first position to a second position which urges or otherwise moves the base plate and the follower plate toward either a buffer core assembly or a partition assembly, depending on the configuration used with the expanding cam lock. The first surface of the base plate and the second surface of the follower plate will contact either an electrophoresis gel cassette of a buffer core assembly or a partition assembly, and thereby sealing the electrophoresis gel cassette to the buffer core assembly. By way of example only, the following configurations may be used, i) the base plate may move toward and the first surface of the base plate may contact an electrophoresis gel cassette of a buffer core assembly, while the follower plate may move toward and the second surface of the follower plate may contact a partition assembly;

ii) the base plate may move toward and the first surface of the base plate may contact a partition assembly, while the follower plate may move toward and the second surface of the follower plate may contact an electrophoresis gel cassette of a buffer core assembly;

iii) the base plate may move toward and the first surface of the base plate may contact an electrophoresis gel cassette of a buffer core assembly, while the follower plate may move toward and the second surface of the follower plate may contact a different electrophoresis gel cassette of a different buffer core assembly; or iv) the base plate may move toward and the first surface of the base plate may contact a partition assembly, while the follower plate may move toward and the second surface of the follower plate may contact a partition assembly.

Additionally, the first surface of the base plate and second surface of the follower plate may include push tabs adapted to facilitate urging of the first surface and the second surface. Also, the first side panels may include slots and the second side panels may include lever arms with locking portions configured to slideably engage the slots.

When the cam is in the second position, the cam may be configured to lock the base plate into engagement with either a partition assembly or an electrophoresis gel cassette of the buffer core and to lock the follower plate into engagement with either a partition assembly or an electrophoresis gel cassette of the buffer core.

The cam of the expanding cam lock incorporated into an electrophoresis assemblies may also include i) at least one push bar configured to engage the base plate to prevent further urging of the first surface toward the buffer core assembly and the second surface toward the partition assembly; ii) at least one handle to pivot the cam relative to the base plate and follower plate; and/or iii) a curved end that slidingly engages the follower plate.

The components of such electrophoresis assemblies, including but not limited to, the electrophoresis container, the base plate, the follower plate, the cam, the partition assembly or the buffer core assembly may be made of various materials, such as polymers, metals, or combinations thereof. The polymer used may be selected from the group consisting of styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate these components include, but are not limited to epoxy based polymers, cyclo-olefin copolymer (COC), polychlorotrifluoroethylene (PCTFE), polyetheretherketone (PEEK), polyetherimide (PEI), polyethersulfone (PES), polyethylene (PE), high density polyethylene (HDPE), low density polyethylene (LDPE), polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinylfluoride (PVF), polyvinylidenechloride (PVDC), polybutyleneterephthalate (PBT), fluorinated ethylenepropylene (FEP), perfluoralkoxyalkane (PFA), and polyvinylidenefluoride (PVDF).

In addition, the components of such electrophoresis assemblies, including but not limited to, the electrophoresis container, the base plate, the follower plate, the cam, the partition assembly or the buffer core assembly may be fabricated by molding techniques, hot embossing methods, casting processes, thermoforming methods, stereolithography processes, machining methods and milling processes. Such molding methods include, but are not limited to, injection molding and compression molding.

Buffer Displacement Dam

In another aspect of the invention, a buffer displacement dam is provided that fits inside a gel electrophoresis apparatus or electrophoretic gel transfer apparatus buffer reservoir and occupies space that, during the use of the apparatus, would otherwise be taken up by buffer. A gel electrophoresis apparatus or electrophoretic transfer apparatus that includes a buffer displacement dam therefore uses less buffer than it would use without a buffer displacement dam. For example, when inserted into a buffer reservoir, a buffer displacement dam can displace 10% or more of buffer that would otherwise be used in an electrophoresis apparatus or electrophoretic transfer apparatus during electrophoresis or electroblotting. Preferably, a buffer displacement dam replaces 20% or more of buffer that would otherwise be used in an electrophoresis apparatus or electrophoretic transfer apparatus, more preferably 30% or more, and more preferably yet 40% or more of buffer that would otherwise be used in an electrophoresis apparatus or electrophoretic transfer apparatus.

A buffer displacement dam used to displace electrophoresis buffer or transfer buffer fits into a buffer reservoir such that it conforms in size to the reservoir in at least one dimension. In other words, at least one side or wall of a buffer displacement dam spans the width or length of a buffer reservoir or aligns along at least one wall or side of a buffer reservoir when the displacement dam is inserted into the buffer reservoir. Preferably, a buffer displacement dam has the same depth as the buffer reservoir it inserts into, but this is not necessarily the case. Preferably a buffer displacement dam according to the present invention fits into the tank such that it stays in a fixed position within the tank. For example, the displacement dam can slide into the tank and be fixed in position by means of grooves, ridges, flanged edges along the top of the sides of the displacement dam, or even clips, cam locks or other fasteners. In a preferred embodiment, however, a buffer displacement dam conforms to the inner dimensions of at least a portion of a buffer tank such that it can be slid into the buffer tank where it fits snugly without requiring additional structures for attachment. For example, a buffer displacement dam can have dimensions such that it fits one end of a buffer reservoir by conforming to the interior of a curved wall of the buffer reservoir or to the interior of two or more non-curved walls of the buffer reservoir such that it fits within the buffer reservoir to remain in a fixed position within the tank. A buffer displacement dam is preferably of the same height as the buffer reservoir it fits into, although this is not a requirement of the present invention. The buffer tank can optionally have a lip or handle that extends beyond the outer edge of one or more areas of the buffer reservoir it fits into that can facilitate insertion and removal of the buffer displacement dam.

Figure 7:
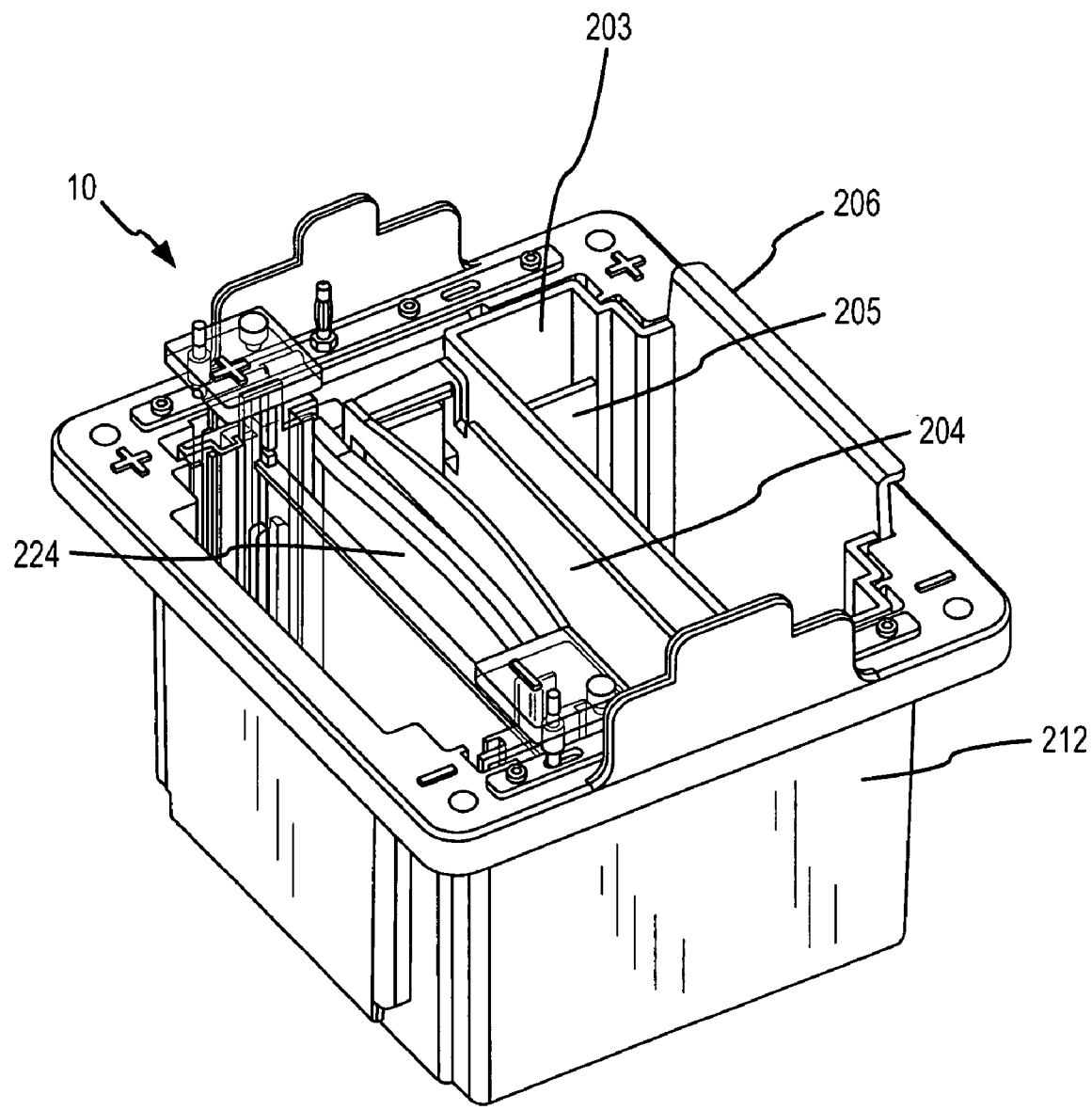
FIG. 7 is a depiction of a gel electrophoresis apparatus that includes a buffer displacement dam.

In some preferred embodiments, a buffer displacement dam has at least four sides and conforms to the dimensions of a buffer reservoir in that at least three of the sides align along the interior of sides of the buffer reservoir such that the buffer displacement dam fits one end of a buffer reservoir, such that when the buffer displacement dam is positioned in the buffer reservoir, the buffer dam fills space that would otherwise be taken up by buffer during the use of the gel electrophoresis or electrophoretic transfer apparatus. For example, FIG. 7 depicts a buffer displacement dam having four sides, in which three of the sides align along the interior of one end of a buffer reservoir. Although not visible in the figure, the bottom of the displacement dam shown aligns along the bottom of the buffer reservoir (gel system container).

Although a buffer displacement dam conforms to the interior dimensions of at least a portion of a buffer reservoir, it need not conform precisely. For example, it may not have a shape that fits into grooves or minor indentations of a buffer reservoir. Essentially, a displacement dam should conform to the interior dimensions of at least a portion of a buffer reservoir such that it fits the buffer reservoir sufficiently closely that it stays in position without bobbing or sliding out of position in the tank, but not so tightly that it is difficult to insert and remove.

A buffer displacement dam can be solid but is preferably at least partially hollow, making the buffer displacer lighter and less expensive to manufacture than a solid piece. For example, a buffer displacement dam can comprise a bottom and a curved circumference or curved or noncurved sides, in which the circumference or sides of the buffer displacement dam conforms to the inner dimensions of at least a portion of a buffer reservoir, and the circumference or sides are in the form of a wall or walls that define an interior space. The sides or walls can be straight or curved, and regular or irregular in shape. A buffer displacement dam can have a single wall that is curved to circumscribe a circular, ovoid, or other regular or irregular curved shape. The displacement dam can have one or more internal walls or support structures for structural support. The buffer displacement dam is preferably open at the top, although this is not a requirement of the invention.

The buffer displacement dam may be fabricated from materials which are fluid-impermeable and non-conducting. By way of example only, such suitable materials, include polymeric materials may be fabricated from various polymeric materials. Such polymers include, but not limited to, styrene acrylonitrile (SAN), polyurethane, polyvinylchloride (PVC), polycarbonate, polystyrene (PS), acrylic-based polymers, nylon based polymers, polymethylmethacrylate (PMMA), polyethylene terephthalate (PET), glycol-modified polyethylene terephthalate (PETG), polypropylene (PP), cyclo-olefin polymer (COP), polyphenylene ether (PPE), polyoxymethylene (POM), and copolymers thereof. Other representative materials that can be used to fabricate the gel cassette adaptor 30 include, but are not limited to epoxy based polymers, cyclo-olefin copolymer (COC), polychlorotrifluoroethylene (PCTFE), polyetheretherketone (PEEK), polyetherimide (PEI), polyethersulfone (PES), polyethylene (PE), high density polyethylene (HDPE), low density polyethylene (LDPE), polyethylene naphthalate (PEN), polyester, polyhydroxybutyrate (PHB), polyhydroxyvalerate copolymer, polyimide (PI), polyoxymethylene copolymer (POMC), polyoxymethylene copolymer (POMC), polyoxymethylene homopolymer (POMH), polyphenyleneoxide (PPO), polyphenylenesulfide (PPS), polyphenylsulfone (PPSu), polystyrol, polysulphone (PSu), polytetrafluoroethylene (PTFE), polyvinylfluoride (PVF), polyvinylidenechloride (PVDC), polybutyleneterephthalate (PBT), fluorinated ethylenepropylene (FEP), perfluoralkoxyalkane (PFA), and polyvinylidenefluoride (PVDF).

In addition the buffer displacement dam may be fabricated using molding techniques, hot embossing methods, casting processes, thermoforming methods, stereolithography processes, machining methods and milling processes. Such molding techniques include, but are not limited to, injection molded and compression molding.

A displacement dam can be used, for example, in a "wet" electroblotting apparatus to occupy space in the buffer reservoir that would otherwise be taken up by transfer buffer. A displacement dam designed for use in an electroblotter is designed to fit into a buffer reservoir (buffer tank) that holds one or more gel cassettes, such that its position does not interfere with the passage of electrical current through the one or more gel cassettes inserted in the electroblotting device.

In one example, an electrophoretic transfer apparatus that is designed for transferring biomolecules (such as but not limited to proteins or nucleic acids) from a gel to a membrane or filter can be designed to hold a gel cassette of a particular "standard" size in a buffer reservoir or tank, but can also hold a smaller than standard size gel cassette. In the context of electroblotting, a gel cassette is a structure having two sides that enclose a gel and a transfer membrane or filter. The sides of an electroblotting cassette are porous, meshed, latticed, or otherwise permeable to fluid to allow the passage of buffer and electrical current from one side of the electroblot cassette, through the gel and transfer membrane, to the other side of the electroblot cassette. In cases in which a smaller than standard size cassette is used in the electroblotter, a buffer displacement dam can be inserted into the buffer tank to reduce the amount of buffer used during electrophoretic transfer.

In another example, an electrophoretic transfer apparatus that is designed for transferring biomolecules (such as but not limited to proteins or nucleic acids) from a gel to a membrane or filter can be designed to hold multiple gel cassettes in a buffer reservoir or tank, but can also hold fewer than the maximum number of gel cassettes it is designed to hold. In cases in which fewer than the maximum number of cassettes are used in the electroblotter, a buffer displacement dam can be inserted into the buffer tank to reduce the amount of buffer used during electrophoretic transfer. When inserted into the buffer tank of an electroblotting apparatus, the buffer displacement dam can optionally occupy the space the position that would be taken by one or more additional cassettes, if the maximum number of cassettes were used in the apparatus.

The present invention includes an electrophoretic transfer apparatus that includes a buffer tank, in which the buffer tank comprises or contacts two electrodes and comprises a buffer displacement dam and at least one gel cassette that comprises a gel and a transfer membrane. The buffer displacement dam can displace at least 10%, preferably at least 20%, and more preferably at least 30% of the volume of transfer buffer that would otherwise be held by the buffer tank. In some embodiments, the displacement dam can displace 40% or more of the volume of transfer buffer that would otherwise be held by the buffer tank.

The invention also includes a method of electrophoretically transferring one or more biomolecules from a gel to a transfer membrane or filter using a displacement dam in the buffer tank of an electrophoretic transfer apparatus, in which the electrophoretic transfer uses less transfer buffer that the maximum amount of buffer that can be accommodated by the buffer tank. The method includes: positioning an electrophoretic transfer gel cassette that comprises a gel containing one or more biomolecules and a transfer membrane in a buffer tank of an electrophoretic transfer apparatus; inserting a buffer displacement dam into the buffer tank; adding transfer buffer to the buffer tank; connecting a power source to electrodes within or connected to the buffer tank, and applying a voltage across the cassette to transfer biomolecules from the gel to the transfer membrane. The method uses less transfer buffer than would be used in the absence of a buffer displacement dam. The method can be used when a smaller cassette is used than the standard size accommodated by a transfer apparatus, or when fewer than the maximal number of cassettes are used in the apparatus. The use of the displacement dam is not limited to these circumstances, however. In some cases, a buffer displacement dam can be used when less than maximal amounts of buffer are required based on electrophoretic conditions (buffer composition or applied voltage, e.g.).

A buffer displacement dam can be used in gel electrophoresis apparatuses. The electrophoresis apparatuses can be configured for horizontal or vertical gel electrophoresis. A buffer displacement dam can be used in a cathode buffer reservoir, an anode buffer reservoir, or both an anode buffer reservoir and a cathode buffer reservoir. The gel electrophoresis apparatus can be used for the separation of biomolecules, such as but not limited to proteins, peptides, and nucleic acids.

In some preferred embodiments of the invention, a buffer dam is used in an electrophoresis apparatus that comprises one or more gel cassettes in a vertical orientation, each of which comprises a gel, in which one end of the gel contacts an "upper" buffer reservoir and the other end of the gel contacts a "lower" buffer reservoir. A displacement dam can be used in the apparatus to take the place of one or more cassettes and/or additional buffer reservoirs or buffer cores.

The present invention includes a buffer displacement dam for replacing electrophoresis buffer in an electrophoresis apparatus having a tank, an anode reservoir, and a cathode reservoir, wherein the buffer dam comprises non-conductive material and is positioned within a tank of the electrophoresis apparatus in a position otherwise occupied by a buffer core, such that less than 90%, and preferably less than 75%, of the buffer is necessary within either the anode reservoir or the cathode reservoir compared to the amount of buffer required in the absence of the buffer displacement dam.

One configuration of a gel apparatus comprises a container into which is inserted multiple buffer cores, as depicted in FIG. 1. A gel cassette is sealed to either side of a buffer core to form a buffer core assembly having an internal space that serves as an "upper" buffer reservoir. The area of the container outside the buffer core assembly serves as the "lower" buffer reservoir. When fewer than the maximal number of buffer cores are used in the apparatus, a buffer displacement dam can be inserted into the container to displace buffer that is not required when running fewer than the maximal number of gels in the apparatus.

The buffer displacement dam takes up space in the container of the apparatus that would otherwise be taken up by "lower chamber" running buffer during use of the apparatus. In this way, the buffer displacement dam avoids the unnecessary use of large volumes of buffer when fewer than the maximum number of gels that can be accommodated by the gel system are being run. In preferred aspects of the present invention, a buffer displacement dam can be used in a gel electrophoresis apparatus that can accommodate multiple buffer cores, and the buffer displacement dam occupies at least a portion of the area that would otherwise be taken up by a buffer core, and further replaces volume in the container that would otherwise be taken up by buffer in the "lower reservoir" container (for example, anode buffer).

When the buffer displacement dam is positioned in the gel system container, it is not necessary that it form a seal against the container or a buffer core element to prevent the passage of buffer from one area of the container to another area of the container, because the dam reduces the volume of buffer needed by replacing volume, rather than by blocking off an area of a buffer reservoir. Thus, in alternative embodiments, a buffer displacement dam does not function as a dam, in that it does not perform the function of sealing buffer within a compartment. A convenient feature of a preferred design of a buffer displacement device is that it need not be sealed to one or more walls or edges of a buffer tank. This avoids the use of gaskets or other sealing components, fasteners, etc. A further advantage of this design therefore is that only a single piece is required, and no assembly is performed.

One example of a gel system that can accommodate multiple buffer core assemblies and can use a buffer displacement dam is depicted in FIG. 7. The gel electrophoresis system (10) is made up of a container (212) into which two buffer core assemblies can be inserted. As shown, however, the container (212) holds a single buffer core assembly (224) and a buffer displacement dam (203). The buffer displacement dam (203) conforms to the internal dimensions of one end of the container (212), having four walls that define an interior space. Interior walls of which one is shown (205), provide structural support. The displacement dam (203) also has a lip (206) on the upper edge of one side to facilitate insertion and removal of the displacement dam.

Figure 8A:
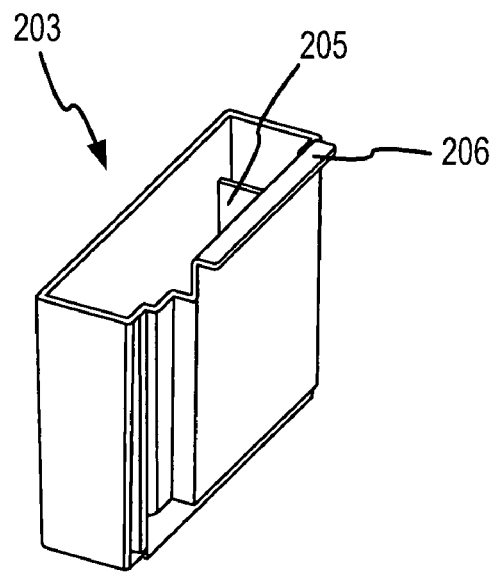
FIG. 8 shows two views of one example of a buffer displacement dam of the present invention. A) perspective view B) side cross-sectional view.
Figure 8B:
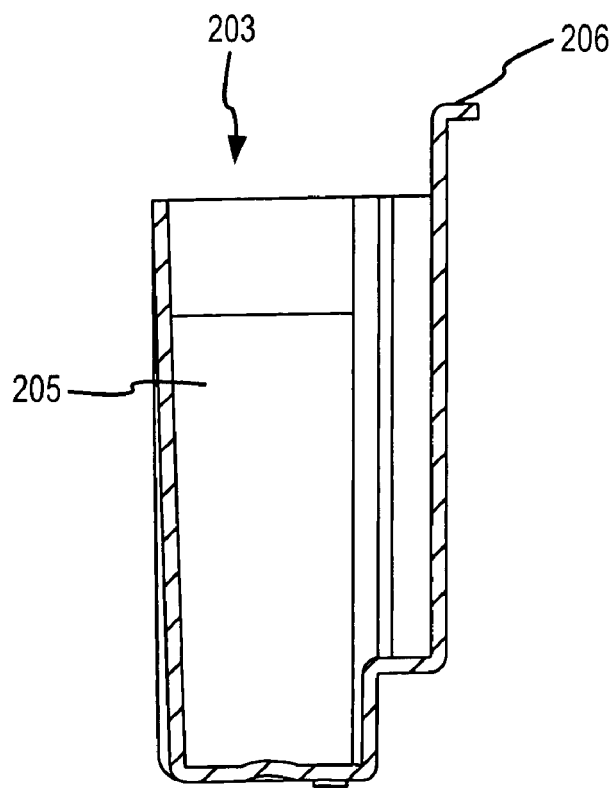

FIG. 8 shows two views of a displacement dam shown separate from the gel electrophoresis system. The displacement dam (203) is shown having four walls and a bottom, in which the protrusions (218) of one of the walls designed to fit the internal dimensions of the container can be seen.

A buffer displacement dam for use in a gel electrophoresis system may be, for example, from about 3 to about 30 inches in height, from about 3 to about 20 inches in height, or preferably, from about 3 to about 10 inches in height (depending on the height of the apparatus), more preferably from about 3 to about 6 inches in height, more preferably yet from about 3.5 to about 5 inches in height, more preferably yet the height is about 4.5 inches. A buffer displacement dam can be from about 4 to about 40 inches in length, or preferably, from about 4 to about 30 inches in length, or preferably, from about 4 to about 20 inches in length, or preferably, from about 4 to about 10 inches in length, more preferably from about 4 to about 8 inches in length, more preferably yet from about 3.5 to about 6.5 inches in length, more preferably yet the length is about 6.14 inches. A buffer displacement dam can be from about 1 to about 25 inches in width, or preferably, from 1 to about 20 inches in width, or preferably, from 1 to about 15 inches in width, or preferably, from 1 to about 10 inches in width, or preferably, from about 1 to about 5 inches in width, or preferably, from about 1 to about 3 inches in width, or preferably, the buffer displacement dam is 1.66 inches in width. The displacement dam can displace any amount of buffer from a buffer reservoir, for example, a volume of from about 50 milliliters to about 1,500 milliliters, from about 100 milliliters to about 1,500 milliliters, from about 200 milliliters to about 1,500 milliliters, or from about 400 milliliters to about 1,000 milliliters. In one example of a buffer displacement dam for use in a midi gel apparatus, the displacement dam replaces from about 500 milliliters to about 750 milliliters of buffer.

Such dimensions and parameters are examples only, as the design of the buffer dam will vary to fit gel apparatus reservoirs in which they are used.

A multiple buffer core gel system can accommodate two, three, or more buffer cores. In some exemplary examples in which a buffer displacement dam takes the place of a buffer core, the gel apparatus is designed to accommodate two buffer core assemblies. For example, the XCell4 SureLock Midi-Cell, designed to run midi (approximately 8 cm×13 cm) gels is an example of a multiple-core electrophoresis system in which a displacement dam can be used. A displacement dam designed to fit the XCell4 SureLock Midi-Cell, as shown in FIGS. 7 and 8, has walls of approximately 4.5 inches in height, is about 6.14 inches in length, and is about 1.66 inches in width. The exemplary displacement dam replaces approximately 675 milliliters of buffer.

In a gel system such as that depicted in FIG. 7, a buffer displacement dam can comprise a wall that can be engaged by a cam lock device for sealing at least one gel cassette to a buffer core in the container occupied by the displacement dam. The cam lock device can optionally be an expanding cam device, as described herein.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

All patents, patent publications, patent applications and other published references mentioned herein are hereby incorporated by reference in their entirety as if each had been individually and specifically incorporated by reference herein.

What is claimed is:

1. An expanding cam lock for sealing at least one gel cassette in an electrophoresis apparatus, the expanding cam lock comprising:
   a base plate having a first surface adapted to engage a buffer core assembly comprising at least one electrophoresis gel cassette;
   a follower plate having a second surface adapted to engage a partition assembly, and
   a cam positioned between and moveably coupled with the base plate and the follower plate;
wherein, the base plate and the follower plate are slideably coupled together and configured for insertion between the buffer core assembly and the partition assembly in the electrophoresis apparatus, and the cam being movable from a first position to a second position to urge the first surface toward the electrophoresis gel cassette of the buffer core assembly and the second surface toward the partition assembly thereby sealing at least one electrophoresis gel cassette to the buffer core assembly within the electrophoresis apparatus.

2. The expanding cam of claim 1, wherein the partition assembly comprises a buffer dam, a buffer displacement dam, or a buffer core assembly comprising at least one electrophoresis gel cassette.

3. The expanding cam of claim 1, wherein the partition assembly comprises a buffer core assembly comprising at least one electrophoresis gel cassette.

4. The expanding cam lock of claim 1, wherein the cam is pivotally coupled to the base plate and is configured to slideably engage the follower plate.

5. The expanding cam lock of claim 4, wherein the cam includes axle pins pivotally coupling the cam to the base plate.

6. The expanding cam lock of claim 1, wherein the cam is configured to lock the base plate into engagement with the electrophoresis gel cassette of the buffer core and the follower plate into engagement with the partition assembly when the cam is in the second position.

7. The expanding cam lock of claim 1, wherein the cam includes a push bar configured to engage the base plate to prevent further urging of the first surface toward the buffer core assembly and the second surface toward the partition assembly.

8. The expanding cam lock of claim 1 wherein the cam includes a handle to pivot the cam relative to the base plate and the follower plate.

9. The expanding cam lock of claim 1, wherein the cam further has a curved end that slidingly engages the follower plate.

10. The expanding cam lock of claim 1, wherein the first and the second surfaces include push tabs adapted to facilitate urging of the first surface toward the buffer core assembly and the second surface toward the partition assembly.

11. The expanding cam lock of claim 1, wherein the base plate includes first side panels on a reverse side opposing the first surface and the follower plate includes second side panels on a reverse side opposing the second surface, the first and the second side panels being coupled together.

12. The expanding cam lock of claim 11, wherein the first side panels include slots and the second side panels include lever arms with locking portions configured to slideably engage the slots.

13. The expanding cam lock of claim 1, wherein at least one of the base plate, the follower plate and the cam is made of a polymer selected from the group consisting of styrene acrylonitrile, polycarbonate, polystyrene, acrylic, acrylate, polymethyl methacrylate, polyethylene, high density polyethylene, polyethylene terephthalate, glycol-modified polyethylene terephthalate, polypropylene, polyoxymethylene, Acetel and copolymers thereof.

14. An electrophoresis kit, comprising
   a) an electrophoresis container having a first end wall defining a first recess and a second end wall defining a second recess;
   b) at least one buffer core assembly; and
   c) an expanding cam lock, comprising:
      a base plate having a first surface adapted to engage a buffer core assembly and having first side panels on the reverse side of the first surface;
      a follower plate having a second surface adapted to engage a partition assembly and having second side panels on the reverse side of the second surface, the first and second side panels being slideably coupled and the base plate and follower plate being configured for insertion between the first buffer core assembly and the partition assembly; and
      a cam pivotally coupled to the base plate and the cam slidingly engaging the follower plate wherein the cam is positioned between the base plate and the follower plate.

15. The electrophoresis kit of claim 14, wherein the partition assembly comprises a buffer dam, a buffer displacement dam, or a buffer core assembly comprising at least one electrophoresis gel cassette.

16. The electrophoresis kit of claim 15, wherein the partition assembly comprises a buffer core assembly comprising at least one electrophoresis gel cassette.

17. The electrophoresis kit of claim 14, wherein at least one of the electrophoresis container, the base plate, the follower plate, the cam, the partition assembly and the buffer core assembly is made of a polymer selected from the group consisting of styrene acrylonitrile, polycarbonate, polystyrene, acrylic, acrylate, polymethyl methacrylate, polyethylene, high density polyethylene, polyethylene terephthalate, glycol-modified polyethylene terephthalate, polypropylene, polyoxymethylene, Acetel and copolymers thereof.

18. The electrophoresis kit of claim 14, wherein the cam includes axle pins pivotally coupling the cam to the base plate.

19. The electrophoresis kit of claim 14, wherein the cam is configured to lock the base plate into engagement with the electrophoresis gel cassette of the buffer core and to lock the follower plate into engagement with the partition assembly when the cam is in the second position.

20. The electrophoresis kit of claim 14, wherein the cam includes a push bar configured to engage the base plate to prevent further urging of the first surface toward the buffer core assembly and the second surface toward the partition assembly.

21. The electrophoresis kit of claim 14, wherein the cam includes a handle to pivot the cam relative to the base plate and the follower plate.

22. The electrophoresis kit of claim 14, wherein the cam further comprises a curved end that slidingly engages the follower plate.

23. The electrophoresis kit of claim 14, wherein the first and the second surfaces include push tabs adapted to facilitate urging of the first surface toward the buffer core assembly and the second surface toward the partition assembly.

24. The electrophoresis kit of claim 14, wherein the first side panels include slots and the second side panels include lever arms with locking portions configured to slideably engage the slots.

25. A method for securing an electrophoresis gel cassettes in an electrophoresis container, the method comprising:
   providing a base plate having a first surface adapted to engage a buffer core assembly comprising the electrophoresis gel cassette;
   providing a follower plate having second surface adapted to engage a partition assembly, the follower plate being slideably coupled to the base plate;
   providing a cam positioned between and moveably coupled with the base plate and the follower plate;
   inserting the base plate, the follower plate and the cam between the buffer core assembly and the partition assembly in the electrophoresis container;
   moving the cam from an open position to a closed position to urge the first and second surfaces to secure the gel cassettes to the buffer core assembly and partition assembly.

26. The method of claim 25, wherein moving the cam to the closed position causes the cam to lock the base plate and the following plate into engagement with the gel cassettes of the buffer core assembly and partition assembly.

27. The method of claim 25, wherein the partition assembly comprises a buffer dam, a buffer displacement dam, or a buffer core assembly comprising at least one electrophoresis gel cassette.

28. The method of claim 27, wherein the partition assembly comprises a buffer core assembly comprising at least one electrophoresis gel cassette.

* * * * *